United States Patent
Lu et al.

(10) Patent No.: US 7,803,356 B2
(45) Date of Patent: Sep. 28, 2010

(54) COMPOSITIONS CONTAINING AT LEAST ONE SILICONE RESIN AND A VOLATILE NON-CYCLIC SILICONE OIL

(75) Inventors: Shao Xiang Lu, Plainsboro, NJ (US); Mohammed Kanji, Edison, NJ (US)

(73) Assignee: L'Oreal, Paris (FR)

( * ) Notice: Subject to any disclaimer, the term of this patent is extended or adjusted under 35 U.S.C. 154(b) by 1257 days.

(21) Appl. No.: 11/008,164

(22) Filed: Dec. 10, 2004

(65) Prior Publication Data
US 2005/0142089 A1 Jun. 30, 2005

Related U.S. Application Data

(60) Provisional application No. 60/528,696, filed on Dec. 12, 2003.

(51) Int. Cl.
*A61Q 1/04* (2006.01)
*A61Q 1/08* (2006.01)

(52) U.S. Cl. .............................. 424/64; 424/63; 424/401
(58) Field of Classification Search ..................... None
See application file for complete search history.

(56) References Cited

U.S. PATENT DOCUMENTS

| 5,837,223 | A | * | 11/1998 | Barone et al. | ............... | 424/64 |
| 6,162,421 | A | * | 12/2000 | Ordino et al. | ................. | 424/64 |
| 6,326,013 | B1 | * | 12/2001 | Lemann et al. | ............ | 424/401 |
| 6,958,155 | B2 | * | 10/2005 | Lu et al. | ..................... | 424/401 |

FOREIGN PATENT DOCUMENTS

| EP | 1082953 | * | 3/2001 |
| WO | WO 03/105789 | * | 12/2003 |

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

The present invention generally relates to compositions containing at least one silicone resin, and at least one volatile non-cyclic silicone oil.

19 Claims, No Drawings

COMPOSITIONS CONTAINING AT LEAST ONE SILICONE RESIN AND A VOLATILE NON-CYCLIC SILICONE OIL

BACKGROUND OF THE INVENTION

1. Field of the Invention

The present invention generally relates to compositions containing at least one silicone resin and at least one volatile non-cyclic silicone oil.

2. Discussion of the Background

Many compositions, including pigmented cosmetic compositions (such as, for example, foundations, mascaras, lip compositions, eyeliners, etc.) and non-pigmented cosmetic compositions (such as, for example, moisturizers, sunscreens, etc.), attempt to provide longer wear and transfer resistance. Compositions which form a film after application may exhibit such properties. Generally, film forming compositions contain volatile solvents which evaporate on contact with the skin or other keratinous material, and leave behind a layer comprising waxes and/or resins, and any pigments, fillers and active agents that may be in the composition.

Different types of polymers have been used in an attempt to achieve such film formation. One such type of polymer is silicone resin.

Certain polymethylsilsesquioxanes have previously been used in hair care compositions. See, e.g., U.S. Pat. No. 5,246,694 which discloses a shampoo composition comprising a surfactant, an aqueous emulsion of highly viscous silicone in volatile silicone and a cationic polymer which is a derivative of guar gum.

Similarly, U.S. Pat. No. 5,439,673 discloses the use of silicone resins in a hair care composition. The resins disclosed therein include Resin MK and Resin MQ. Further, EP 0 560 879 B1 discloses the use of similar resins (MQ, MT, MTQ, and MDTQ resins) in hair conditioning compositions.

The use of certain silicone polymers or derivatives thereof in cosmetic compositions has also been disclosed. See e.g., U.S. Pat. Nos. 5,965,112; 5,800,816; 5,911,974; and 5,959,009. However, these compositions may be uncomfortable to wear as the composition that remains on the skin or other keratinous material may be a brittle or non-flexible film. These compositions may also tend to flake off the skin or other keratinous material due to poor adhesion to the material. Furthermore, prior to application, these compositions may be tacky, which may result in poor application and spreadability characteristics.

There is, therefore, a need for improved compositions such as long wearing cosmetic compositions which limit transfer to other materials such as, for example, skin or fabric, i.e., transfer resistant compositions, which also possess good cosmetic properties such as, for example, wearing comfort and waterproof properties, and which are not tacky or "draggy" during and after application.

SUMMARY OF THE INVENTION

The present invention relates to compositions, preferably cosmetic compositions, comprising at least one silicone resin and at least one volatile non-cyclic silicone oil, as well as to methods for treating, caring for and/or making up keratinous material by applying such compositions to the keratinous material.

The present invention also relates to cosmetic compositions comprising at least one volatile non-cyclic silicone oil, at least one polymethylsilsesquioxane film forming agent and at least one MQ resin.

The present invention further relates to pigmented cosmetic compositions comprising at least one volatile non-cyclic silicone oil, at least one polymethylsilsesquioxane film forming agent and at least one MQ resin.

The present invention also relates to anhydrous pigmented cosmetic compositions comprising at least one volatile non-cyclic silicone oil, at least one polymethylsilsesquioxane film forming agent and at least one MQ resin. Preferably, such anhydrous pigmented cosmetic compositions are lip compositions (for example, lipstick) or foundations.

The present invention further relates to pigmented cosmetic compositions comprising at least one volatile non-cyclic silicone oil, at least one polymethylsilsesquioxane film forming agent, at least one MQ resin and water. Preferably, such water-containing pigmented cosmetic compositions are lip compositions (for example, lipstick), foundations or mascaras, and are emulsions or dispersions.

The present invention also relates to methods of treating, caring for and/or making up keratinous material (for example, skin) by applying compositions of the present invention to the keratinous material in an amount sufficient to treat, care for and/or make up the keratinous material.

The present invention further relates to covering or hiding skin defects associated with keratinous material (for example, skin) by applying compositions of the present invention to the keratinous material in an amount sufficient to cover or hide such skin defects.

The present invention also relates to methods of enhancing the appearance of keratinous material (for example, skin) by applying compositions of the present invention to the keratinous material in an amount sufficient to enhance the appearance of the keratinous material.

The present invention further relates to compositions having improved cosmetic properties such as, for example, improved long wear, transfer resistance or waterproof properties. The compositions may also possess improved flexibility, wearability, drying time, retention, tackiness (low), and migration over time (low).

DETAILED DESCRIPTION OF THE INVENTION

"At least one" as used herein means one or more and thus includes individual components as well as mixtures/combinations.

"Film former" as used herein means a polymer that, after dissolution in at least one solvent (such as, for example, water and organic solvents), leaves a film on the substrate to which it is applied once the at least one solvent evaporates.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. In one embodiment, little or no composition is transferred to the substrate. Further, the amount transferred may be compared with that transferred by other compositions, such as commercially available compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In one embodiment, little or no composition is transferred from the wearer.

In accordance with certain aspects of the present invention, the phrase "liquid fatty phase" is understood to mean a fatty phase, which is liquid at room temperature (25° C.) and atmospheric pressure (760 mmHg), and which comprises one or more fatty substances that are liquid at room temperature, also known as oils, which are compatible with one another.

In accordance with certain aspects of the present invention, the phrase "structured liquid fatty phase" is understood to mean that this structured phase does not run between the fingers and is at least thickened.

Where the liquid fatty phase is structured, it makes it possible to limit exudation of the fatty phase from solid compositions, and furthermore, to limit, after deposition on the skin or the lips, its migration into the wrinkles and fine lines, which is desired for compositions such as a lipstick or an eyeshadow. Significant migration of the liquid fatty phase, laden with coloring materials, leads to an unaesthetic effect around the lips or the eyes, which can accentuate the wrinkles and fine lines. This migration is often mentioned by women as being a major defect of conventional lipsticks and eyeshadows. The term "migration" is understood to mean running of the composition deposited on the lips or skin beyond its initial outline.

"Gloss" is essentially related to the nature of the liquid fatty phase. Thus, it is possible to reduce the level of waxes and fillers in the composition in order to increase the gloss of a lipstick, but then the migration of the liquid fatty phase increases. In other words, the levels of waxes and/or of fillers necessary for preparation of a stick of suitable hardness have been a restricting factor on the gloss of the deposit.

"Tackiness" as used herein refers to measuring the maximum tensile force, $F_{max}$, required while separating two surfaces. Depending on the application envisaged and the formulation being designed, the desirable value for $F_{max}$ may vary. In some embodiments, the substantially non-tacky compositions have a $F_{max}$ of less than about 4 Newton (N), less than about 1 N, less than about 0.5 N, less than about 0.3 N, less than about 0.2 N or less than 0.1 N. One of ordinary skill in the art can determine the $F_{max}$ of the composition by, for example, determining the maximum force of traction, measured with an extensiometer of the LLOYD model LR5K type, needed to detach two surfaces.

For example, two 38 mm$^2$ surfaces, A and B, which are solid, rigid, inert, and non-absorbing, are mounted on movable mounts, facing each other. The surfaces may be movable either toward or away from each other, or one may move surface A independently from surface B or vice versa. Prior to insertion into the extensiometer, surface A is coated with the composition to be measured, which may be dissolved in a solvent such as aqueous, hydroalcoholic, hydrocarbon, silicone, and alcoholic solvents in a concentration of from about 10 to about 30%, preferably 20%, the surface A is coated in a thickness of from 1 to 10 mil, preferably 1 mil, and the surface is dried for 24 hours at room temperature, e.g., 22 to 25° C., at a relative humidity of about 50%. Once inserted in the extensiometer, surface A is subjected for 20 seconds to a compression force of 3 N against surface B and then subjected for 30 seconds to tensile force at a rate of 20 mm/minute. The amount of force, $F_{max}$, needed to obtain initial separation is then noted. A mean $F_{max}$ is determined by carrying out the procedure with multiple pairs, preferably at least six pairs, of surface A and surface B.

The composition of the present invention may be in any form. For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The composition can also be in a form chosen from a translucent anhydrous gel and a transparent anhydrous gel. The composition of the invention may, for example, comprise an external or continuous fatty phase. The composition may be anhydrous. In another embodiment, the composition of the invention may be transparent or clear, including for example, a composition without pigments. The composition can also be a molded composition or cast as a stick or a dish. The composition in one embodiment is a solid such as a molded stick or a poured stick. The compositions of the present invention may also be in the form a lip composition such as a lipstick or a liquid lip color, a foundation or a mascara, which exhibit excellent and improved properties of transfer-resistance, flexibility, pliability, adherence and lack of tackiness.

Where the composition of the invention is not-liquid, the structuring of the liquid fatty phase can be controlled by one or more structuring polymers and is such that a rigid structure in the form of a stick, of good mechanical resistance, can be obtained. These rigid compositions, when colored, allow for a supple, light, non-transfer, non-migrating and/or long-wearing applications on a keratinous surface. Such compositions may contain one or more structuring polymers.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 40° C., 37° C., 45° C., 50° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on a keratinous material. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As is evident, the hardness of the composition according to preferred embodiments of the invention may, for example, be such that the composition is advantageously self-supporting and can disintegrate easily to form a satisfactory deposit on the skin and/or the lips and/or superficial body growths, such as keratinous fibers. In addition, with this hardness, the composition of the invention may have good impact strength.

According to preferred embodiments of the present invention, the composition in stick form may have the behavior of a deformable, flexible elastic solid, giving noteworthy elastic softness on application. The compositions in stick form of the prior art do not have these properties of elasticity and flexibility.

Liquid Fatty Phase

According to preferred embodiments of the present invention, cosmetic compositions comprising at least one silicone resin in a liquid fatty phase containing volatile non-cyclic silicone oil are provided. These volatile non-cyclic silicone oils may be branched or linear. For example, volatile non-cyclic silicone oils that may be used in the compositions of the present invention include those described in U.S. Pat. No. 6,338,839 and WO03/042221, the contents of which are incorporated herein by reference. In one embodiment the volatile non-cyclic silicone oil is ethylheptamethyltrisiloxane or butylheptamethyltrisiloxane. In another embodiment, the ethylheptamethyltrisiloxane or butylheptamethyltrisiloxane is further combined with another solvent that is more volatile than ethylheptamethyltrisiloxane and/or butylheptamethyltrisiloxane. In another embodiment, the volatile non-cyclic silicone oils can be selected from those disclosed in EP 1213006A1, such as, for example an organopolysiloxane having the following general formula: $\{(CH_3)_3SiO\}_3SiCH_3$.

The volatility of the solvents/oils can be determined using the evaporation speed as set forth in U.S. Pat. No. 6,338,839.

In one embodiment, the liquid fatty phase may also comprise, in addition to the volatile non-cyclic silicone, at least one additional volatile oil, e.g., another type of silicone volatile oil, a hydrocarbon volatile oil, or a mixture thereof. In accordance with this embodiment, the liquid fatty phase may contain, in addition to the volatile non-cyclic silicone oil, singularly or in combinations, other volatile silicone oils, non-volatile silicone oils, volatile non-silicone oils and non-volatile non-silicone oils. In one embodiment, the compositions of the present invention are substantially free of silicone oils other than the volatile non-cyclic silicone oils included in the invention (i.e., contain less than about 0.1% silicone oils). In another embodiment, the compositions are substantially free of non-silicone oils (i.e., contain less than about 0.1% non-silicone oils). In another embodiment, the compositions are substantially free of non-volatile oils (i.e., contain less than about 0.1% non-volatile oils).

When volatile oils are present, these volatile oils permit an easier application of the composition on the skin, lips or keratinous fibers.

Examples of volatile silicone oils that may be combined with the non-cyclic silicone oils include, but are not limited to, octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the additional volatile silicone oils have a flash point of at least 40° C. Non-limiting examples of volatile silicone oils are listed in Table 1 below.

TABLE 1

| Compound | Flash Point(° C.) | Viscosity (cSt) |
|---|---|---|
| Octyltrimethicone | 93 | 1.2 |
| Hexyltrimethicone | 79 | 1.2 |

TABLE 1-continued

| Compound | Flash Point (° C.) | Viscosity (cSt) |
|---|---|---|
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Examples of other silicone oils that may be used in the invention include non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

According to other preferred embodiments, the composition may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of other non-silicone oils which can be used in the compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Preferably, the liquid fatty phase, when present, represents from 5% to 98.4% of the total weight of the composition, more preferably from 10% to 80% of the total weight of the composition, and most preferably from 20% to 75%.

Silicone Resins

Silicone resin nomenclature is known in the art as "MDTQ" nomenclature, whereby a silicone resin is described according to the various monomeric siloxane units which make up the polymer. The silicone resins preferably are used as film-forming agents in the compositions of the present invention.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure:

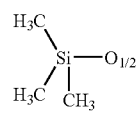

At least one of the methyl groups of the M unit may be replaced by another group, e.g., to give a unit with formula $[R(CH_3)_2]SiO_{1/2}$, as represented in the following structure:

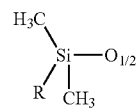

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

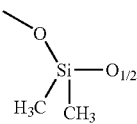

At least one of the methyl groups of the D unit may be replaced by another group, e.g., to give a unit with formula $[R(CH_3)_2]SiO_{1/2}$.

The symbol T denotes the trifunctional unit, $(CH_3)SiO_{3/2}$ and can be represented as:

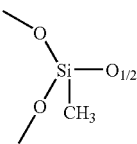

At least one of the methyl groups of the T unit may be replaced by another group, e.g., to give a unit with formula $[R(CH_3)_2]SiO_{1/2}$.

Similarly, the symbol Q denotes the tetrafunctional unit, $SiO_{4/2}$ wherein all four oxygens bonded to the silicone atom are bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include silanes, siloxanes, siloxysilicates, and silsesquioxanes. A non-limiting example of such a siloxane is polydimethylsiloxane (PDMS). Polydimethylsiloxanes are generally composed of long straight chains of $(CH_3)_2SiO_{2/2}$ (i.e., D units) and have viscosities which are dependent on both the size of the polymer and the presence and nature of any substituent(s) on the polymer. A non-limiting example of a siloxysilicate is trimethylsiloxysilicate, which may be represented by the following formula:

$$[(CH_3)_3\text{—}Si\text{—}O]_x\text{—}(SiO_{4/2})_y$$

(i.e., MQ units) wherein x and y may, for example, range from 50 to 80. Silsesquioxanes, on the other hand, may be represented by the following formula:

$$(CH_3SiO_{3/2})_x$$

(i.e., T Units) wherein x may, for example, have a value of up to several thousand.

Polymethylsilsesquioxanes are silsesquioxanes that do not have a substituent replacing the methyl groups. Certain polymethylsilsesquioxanes have previously been used in hair care compositions. See, e.g., U.S. Pat. No. 5,246,694, the disclosure of which is incorporated herein by reference, which discloses a shampoo composition comprising a surfactant, an aqueous emulsion of highly viscous silicone in volatile silicone and a cationic polymer which is a derivative of guar gum. The highly viscous silicone disclosed therein may be chosen from silicone resins including a polymethylsilsesquioxane such as Resin MK (also called SiliconHarz MK) which is available from Wacker, and a siloxysilicate such as Resin MQ which is available from General Electric and Dow Corning.

The Resin MK and Resin MQ silicone resins may form a film after a volatile carrier has evaporated. The MQ film is generally hard and brittle at room temperature, while the MK film is generally continuous and flexible, i.e., not brittle. Depending on the application, plasticizers may be added to help obtain a more flexible, thus more comfortable, film.

In one embodiment, the silicone resin may be a polymethylsilsesquioxane resin such as Belsil PMS MK, also referred to as Resin MK, available from Wacker Chemie. This polymethylsilsesquioxane resin is a polymer comprising polymerized repeating units of $CH_3SiO_{3/2}$ (T units) and may also contain up to 1% by weight or by mole of units of the formula $(CH_3)_2SiO_{2/2}$ (D units). The weight-average molecular weight of this polymer has been estimated to be 10,000. It is believed that the polymers are in a "cage" and "ladder" configuration, as exemplified in the figures below. The majority of the polymer is in the "ladder" configuration, wherein the ends of the polymer are capped with ethoxy $(CH_3CH_2O)$ groups. The ethoxy groups are generally present in an amount of 4.5% by weight and the mole percent is generally 7% (silicone units). As ethoxy groups may react with water, a small and variable amount of SiOH may also be present in the polymer.

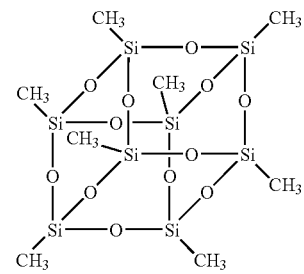

Cage

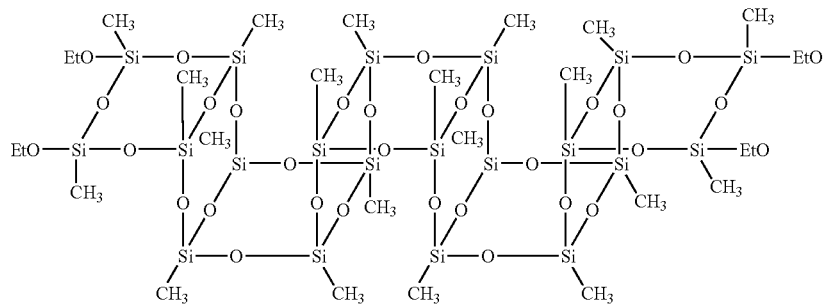

Ladder

Another non-limiting example of the at least one polymethylsilsesquioxane resin suitable for use in the present invention is KR-220L, which is available from SHIN-ETSU. This polymethylsilsesquioxane resin is composed of silicone T-units (i.e., those of formula $CH_3SiO_{3/2}$) and has Si—OH (or silanol) end units. There are no D units in KR-220L.

Other non-limiting examples of the at least one polymethylsilsesquioxane resin that may be useful in the practice of the invention include KR-242A (which is comprised of methyl T units (98%) and dimethyl D units (2%) and has Si—OH end units) and KR-251 (which is comprised of methyl T units (88%) and dimethyl D units (12%) and has Si—OH end units), both of which are available from SHIN-ETSU.

Depending on the application, the concentration of the at least one polymethylsilsesquioxane resin in the presently claimed composition may vary considerably. One of skill in the art will be able to determine routinely the amount of the at least one polymethylsilsesquioxane resin depending on the desired application.

In another embodiment, the silicone resin may be chosen from siloxysilicates. Preferably, the siloxysilicate is trimethylsiloxysilicate, which may or may not be in powder form. Trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Further non-limiting examples of the silicone resins include silicone/(meth)acrylate copolymers, such as those as described in U.S. Pat. Nos. 5,061,481, 5,219,560, and 5,262,087, the disclosures of which are hereby incorporated by reference. Still further non-limiting examples of silicone resins are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Other non-limiting examples of silicone resins suitable for use in the present invention are silicone esters comprising units of formulae (XIV) and (XV), disclosed in U.S. Pat. Nos. 6,045,782, 5,334,737, and 4,725,658, the disclosures of which are hereby incorporated by reference:

$$R_aR^E_bSiO_{[4-(a+b)/2]} \quad \text{(XIV); and}$$

$$R'_xR^E_ySiO_{1/2} \quad \text{(XV)}$$

wherein

R and R', which may be identical or different, are each chosen from optionally substituted hydrocarbon groups;

a and b, which may be identical or different, are each a number ranging from 0 to 3, with the proviso that the sum of a and b is a number ranging from 1 to 3, x and y, which may be identical or different, are each a number ranging from 0 to 3, with the proviso that the sum of x and y is a number ranging from 1 to 3;

$R^E$, which may be identical or different, are each chosen from groups comprising at least one carboxylic ester.

In one embodiment, $R^E$ groups are chosen from groups comprising at least one ester group formed from the reaction of at least one acid and at least one alcohol. In another embodiment, the at least one acid comprises at least two carbon atoms. In another embodiment, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy) propane.

Further non-limiting examples of the at least one silicone resin include liquid sioxy silicates and silicone esters such as those disclosed in U.S. Pat. No. 5,334,737, the disclosure of which is hereby incorporated by reference, such as diisostearoyl trimethylolpropane siloxysilicate and dilauroyl trimethylolpropane siloxy silicate, which are commercially available from General Electric under the tradenames SF 1318 and SF 1312, respectively.

Yet further non-limiting examples of the at least one silicone resin include polymers comprising a backbone chosen from vinyl polymers, methacrylic polymers, and acrylic polymers and at least one chain chosen from pendant siloxane groups and pendant fluorochemical groups. Non-limiting examples of such polymers comprise at least one unit derived from at least one A monomer, at least one unit derived from at least one C monomer, at least one unit derived from D monomers, and, optionally, at least one unit derived from at least one B monomer, wherein:

A, which may be identical or different, are each chosen from free-radically-polymerizable acrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols, and free-radically-polymerizable methacrylic esters of at least one alcoholic hose n from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols;

B, which may be identical or different, are each chosen from reinforcing monomers which are copolymerizable with at least one A monomer;

C, which may be identical or different, are each chosen from monomers having the formula:

$$X(Y)_nSi(R)_{3-m}Z_m$$

wherein

X is chosen from vinyl groups which are copolymerizable with at least one A monomer and at least one B monomer, Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;

n is zero or 1;

m is a number ranging from 1 to 3;

R, which may be identical or different, are each chosen from hydrogen, $C_1$-$C_4$ alkyl groups, aryl groups, and alkoxy groups; and Z, which may be identical or different, are each chosen from monovalent siloxane polymeric groups; and D, which may be identical or different, are each chosen from free-radically-polymerizable acrylate copolymers and free-radically-polymerizable methacrylate copolymers. Such polymers and their manufacture are disclosed in U.S. Pat. Nos. 5,209,924 and 4,972,037, and WO 01/32737, the disclosures of which are hereby incorporated by reference.

Other non-limiting examples of the at least one silicone resin include silicone/acrylate graft terpolymers, for example, those having the formula:

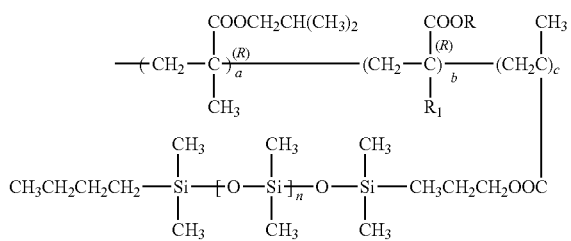

wherein a, b, and c are present in a weight ratio of 69.9:0.1:30 respectively,

R and $R_1$, which may be identical or different, are each chosen from hydrogen and $C_1$-$C_6$ alkyl groups; and m is a number ranging from 100-150.

In an embodiment, m is chosen to provide a macromer having a molecular weight ranging from 8,000 to 12,000, such as 10,000. In another embodiment, m is a number ranging from 124-135, such as 130. Non-limiting examples of these copolymers are described in WO 01/32727 A1, the disclosure of which is hereby incorporated by reference.

Still other examples of suitable silicone resins include copolymers comprising a backbone chosen from vinyl backbones, methacrylic backbones, and acrylic polymeric backbones and further comprising at least one pendant siloxane group. Non-limiting examples of such polymers are disclosed in U.S. Pat. Nos. 4,693,935, 4,981,903, 4,981,902, the disclosures of which are hereby incorporated by reference.

In an embodiment, the at least one copolymer comprises at least one A monomer, at least one C monomer, and, optionally at least one B monomer, wherein the at least one A monomer is chosen from free-radically-polymerizable vinyl monomers, free-radically-polymerizable methacrylate monomers, and free-radically-polymerizable acrylate monomers; the at least one B monomer, if present, is chosen from at least one reinforcing monomer copolymerizable with the at least one A monomer, and the at least one C monomer is chosen from monomers having the formula:

$X(Y)_nSi(R)_{3-m}Z_m$ wherein:

X is chosen from vinyl groups which are copolymerizable with the at least one A monomer and with the at least one B monomer;

Y is chosen from divalent groups;

n is zero or 1;

m is a number ranging from 1 to 3;

R, which may be identical or different, are each chosen from hydrogen, optionally substituted $C_1$-$C_{10}$ alkyl groups, optionally substituted phenyl groups, and optionally substituted $C_1$-$C_{10}$ alkoxy groups; and Z, which may be identical or different, are each chosen from monovalent siloxane polymeric groups.

Non-limiting examples of A monomers include methacrylic acid esters of $C_1$-$C_{12}$ linear alcohols, methacrylic acid esters of $C_1$-$C_{12}$ of branched alcohols, styrene monomers, vinyl esters, vinyl chloride monomers, vinylidene chloride monomers, and acryloyl monomers.

Non-limiting examples of B monomers include acrylic monomers comprising at least one group chosen from hydroxyl, amino, and ionic groups, and methacrylic monomers comprising at least one group chosen from hydroxyl, amino, and ionic groups. Non-limiting examples of ionic groups include quaternary ammonium groups, carboxylate salts, and sulfonic acid salts.

The C monomers are the same as those described for the C monomers in the previous paragraphs.

Other non-limiting examples of the silicone film-former include a copolymer chosen from vinyl-silicone graft copolymers having the following formula and vinyl-silicone block copolymers having the following formula:

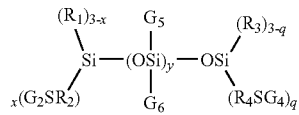

wherein $G_5$, which may be identical or different, are each chosen from alkyl groups, aryl groups, aralkyl groups, alkoxy groups, alkylamino groups, fluoroalkyl groups, hydrogen, and -ZSA groups, wherein A is chosen from vinyl polymeric segments comprising at least one polymerized free-radically-polymerizable monomer, and Z is chosen from divalent $C_1$-$C_{10}$ alkylene groups, divalent aralkylene groups, divalent arylene groups, and divalent alkoxylalkylene groups. In an embodiment Z is chosen from methylene groups and propylene groups.

$G_6$, which may be identical or different, are each chosen from alkyl groups, aryl groups, aralkyl groups, alkoxy groups, alkylamino groups, fluoroalkyl groups, hydrogen, and -ZSA groups, as defined above;

$G_2$ comprises A;

$G_4$ comprises A;

$R_1$, which may be identical or different, are each chosen from alkyl groups, aryl groups, aralkyl groups, alkoxy groups, alkylamino groups, fluoroalkyl groups, hydrogen, and hydroxyl. In one embodiment, $R_1$ is chosen from $C_1$-$C_4$ alkyl groups, such as methyl groups, and hydroxyl.

$R_2$, which may be identical or different, are each chosen from divalent $C_{1-10}$ alkylene groups, divalent arylene groups, divalent aralkylene groups, and divalent alkoxyalkylene groups. In one embodiment, $R_2$ is chosen from divalent $C_1$-$C_3$ alkylene groups and divalent $C_7$-$C_{10}$ aralkylene groups. In another embodiment, $R_2$ is chosen from —$CH_2$— groups and divalent 1,3-propylene groups.

$R_3$, which may be identical or different, are each chosen from alkyl groups, aryl groups, aralkyl groups alkoxy groups, alkylamino groups, fluoroalkyl groups, hydrogen, and hydroxyl. In one embodiment, $R_3$ is chosen from $C_1$-$C_4$ alkyl groups and hydroxyl. In another embodiment, $R_3$ is chosen from methyl groups.

$R_4$, which may be identical or different, are each chosen from divalent $C_1$-$C_{10}$ alkylene groups, divalent arylene groups, divalent aralkylene groups, and divalent alkoxyalkylene groups. In one embodiment, $R_4$ is chosen from divalent $C_1$-$C_3$ alkylene groups and divalent $C_7$-$C_{10}$ aralkylene groups. In another embodiment, $R_4$ is chosen from divalent —$CH_2$— groups and divalent 1,3-propylene groups.

x is a number ranging from 0 to 3;

y is a number greater than or equal to 5. In an embodiment, y ranges from 10 to 270, and in another embodiment, y ranges from 40 to 270.

q is a number ranging from 0 to 3;

Non-limiting examples of these polymers are described in U.S. Pat. No. 5,468,477, the disclosure of which is hereby incorporated by reference. A non-limiting example of such polymers is poly(dimethylsiloxane)-g-poly(isobutyl methacrylate), which is commercially available from 3M Company under the tradename VS 70 IBM.

According to preferred embodiments, the silicone resin is present in the composition in an amount ranging from 0.1% to 30% by weight relative to the total weight of the composition. Preferably, the silicone resin is present in an amount ranging from 0.5% to 20% by weight relative to the total weight of the composition, and more preferably from 1% to 10%. One of ordinary skill in the art will recognize that the silicone resin of the present invention may be commercially available, and may come from suppliers in the form of a dilute solution. The amounts of the silicone resin disclosed herein therefore reflect the weight percent of active material.

According to preferred embodiments, the cosmetic compositions described herein may also contain at least one coloring agent. Preferably, such colored cosmetic compositions are lip compositions (for example, lipstick or liquid lip colors) or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%. In the case of certain products, the pigments, including nacreous pigments, may, for example, represent up to 50% by weight of the composition.

According to preferred embodiments of the present invention, the compositions according to the invention are anhydrous. By "anhydrous," it is meant that the composition contains substantially no water (that is, less than about 0.1% by weight of the composition of water).

According to other preferred embodiments, the compositions according to the invention further comprise water. In this embodiment, water is preferably present in an amount ranging from about 0.1 to about 70%, preferably from about 0.5 to 50%, and more preferably from about 1 to about 30% relative to the total weight of the composition. Preferably, such water-containing cosmetic compositions are lip compositions (for example, lipstick or liquid lip colors), foundations or mascaras, and are emulsions or dispersions.

Additional Additives

The composition of the invention can also comprise any additive usually used in the field under consideration. For example, dispersants such as poly(12-hydroxystearic acid), antioxidants, essential oils, preserving agents, fragrances, waxes, liposoluble polymers that are dispersible in the medium, fillers, neutralizing agents, cosmetic and dermatological active agents such as, for example, emollients, moisturizers, vitamins, essential fatty acids, sunscreens, and mixtures thereof can be added. Further examples of suitable additional components can be found in the references which have been incorporated by reference in this application, including but not limited to the applications from which this application claims priority. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 20% (such as from 0.01% to 20%) relative to the total weight of the composition and further such as from 0.01% to 10% (if present).

Non-limiting examples of such additional components include:

Organogelator

According to the invention, the composition may also comprise at least one organogelator. An organogelator is defined herein to include a non-polymeric organic compound whose molecules may be capable of establishing, between themselves, at least one physical interaction leading to a self-aggregation of the molecules with formation of a macromolecular 3-D network which may be responsible for the gelation of the liquid fatty phase. The network can result from the formation of a network of fibrils (due to the stacking or aggregation of organic-gelling molecules), immobilizing the molecules of the liquid fatty phase. Depending on the nature of the organogelator, the interconnected fibrils have variable dimensions which may range up to one micron, or even several microns. These fibrils may occasionally combine to form strips or columns.

The term "gelation" means a thickening of the medium which may result in a gelatinous consistency and even in a solid, rigid consistency which does not flow under its own weight. The ability to form this network of fibrils, and thus the gelation, depends on the nature (or chemical category) of the organogelator, the nature of the substituents borne by its molecules for a given chemical category, and the nature of the liquid fatty phase. For example, this gelation is reversible.

The physical interactions are diverse but may exclude co-crystallization. These physical interactions are, for instance, interactions chosen from self-complementary hydrogen interactions, π interactions between unsaturated rings, dipolar interactions, and coordination bonding with organometallic derivatives. The establishment of these interactions may often be promoted by the architecture of the molecule, such as by rings, unsaturations, and the presence of asymmetric carbons. In general, each molecule of an organogelator can establish several types of physical interaction with a neighboring molecule. Thus, in one embodiment, the molecules of the organogelator according to the invention may comprise at least one group capable of establishing hydrogen bonding, e.g., at least two groups capable of forming hydrogen bonding; at least one aromatic ring, e.g., at least two aromatic rings; at least one bond with ethylenic unsaturation; and/or at least one asymmetric carbon. The groups capable of forming hydrogen bonding may, for example, be chosen from hydroxyl, carbonyl, amine, carboxylic acid, amide and benzyl groups.

The at least one organogelator of the invention may be soluble in the liquid fatty phase at room temperature and atmospheric pressure. They may be solid or liquid at room temperature and atmospheric pressure.

Organogelator(s) which can be used in the invention are, for example, those described in the document "Specialist Surfactants" edited by D. Robb, 1997, pp. 209-263, chapter 8, by P. Terech, and the French patent application nos. (FR-A-2796276) 99/09178 and 00/09317 (or FR-A-2811552), the disclosures of which are incorporated by reference herein. The organogelators described in these documents are, for example, chosen from:

hydroxylated carboxylic fatty acids having a linear or branched aliphatic carbon chain containing, in one embodiment, at least 8 carbon atoms, such as at least 12 carbon atoms, for instance 12-hydroxystearic acid and 12-hydroxyoleic acid and salts thereof, such as alkali metal salts (in particular Li, Na and K salts) and alkaline-earth metal (for example Mg) salts or esters thereof resulting from esterification of a mono alcohol or polyol having a linear or cyclic, saturated or not chain with from 1 to 6 carbon atoms;

amides of carboxylic acids, such as tricarboxylic acids, for instance the cyclohexanetricarboxamides (see patent application FR-A-2796276, the disclosure of which is incorporated by reference), these amides corresponding, for example, to formula (III) below;

amino acid amides or esters, for instance alanine esters and valine amides (such as those described in the book "Specialist Surfactants");

N-acylamino acid amides, for instance the diamides resulting from the action of an N-acylamino acid with amines containing from 1 to 22 carbon atoms, such as those disclosed in document WO-93/23008, the disclosure of which is incorporated by reference, for example, N-acylglutamides in which the acyl group is a $C_8$ to $C_{22}$ alkyl chain, and N-lauroylglutamic acid dibutylamide, such as the product sold or made by the company Ajinomoto under the name GP-1;

diamides having hydrocarbon-based chains each containing from 1 to 22 carbon atoms, for example, from 6 to 18 carbon atoms, these hydrocarbon-based chains being optionally substituted with ester, urea or fluoro groups (see patent application FR 00/09317, the disclosure of which is incorporated by reference), these diamides being, for example, those of formula (II) hereafter; and such as those resulting from the reaction of diaminocyclohexane, for example, trans-diaminocyclohexane, and of acid chloride;

steroid amines or amides, such as those from deoxycholic acid, cholic acid, apocholic acid or lithocholic acid and salts thereof, for instance D-17,17-dipropyl-17a-aza-5α-homoandrostan-3β-ol or D-17,17-dipropyl-17a-aza-5α-homoandrostan-3 μl-ol 17a-oxy;

compounds containing several aromatic rings (2 or 3), such as anthryl derivatives comprising at least 2 alkyl chains containing from 8 to 30 carbon atoms, for instance 2,3-bis(n-decyloxy)anthracene or 2,3-bis(n-decyloxy)anthraquinone, or comprising a steroid group, for instance cholesteryl 4-(2-anthryloxy)butanoate or cholesteryl anthraquinone-2-carboxylate and derivatives thereof;

azobenzene steroids such as those described in the book "Specialist Surfactants";

organometallic compounds, for instance mononuclear copper β-diketonate (the octasubstituted copper complex of bis(3,4-nonyloxybenzoyl) methanes), binuclear copper tetra-carboxylates or the Zn (II) complexes of trisubstituted (para-carboxyphenyl)porphyrine;

surfactants in salt form comprising at least two linear or branched alkyl chains, such as alkali metal or aluminium alkyl phosphates comprising two alkyl chains containing from 8 to 30 carbon atoms, for instance the aluminium salt of hexadecyl phosphate ($C_{16}$DP-Al) or bis(2-ethylhexyl)phosphate and alkali metal (Na) salts thereof, bis(2-ethylhexyl) sulphosuccinate and the alkali metal (Na) salts thereof;

benzylidene sorbitols or alditols and derivatives thereof, for instance 1,3: 2,4-di-o-benzylidene-D-sorbitol;

cyclodipeptides which are cyclic condensates of two amino acids such as those disclosed in the book "Specialist Surfactants";

cyclic compounds or alkylene compounds comprising two urea or urethane groups such as dialkylurea cyclohexane, having, for example, the formula (IV) below;

alkylaryl cyclohexanol derivatives in which the alkyl chain is linear or branched and comprises from 1 to 22 carbon atoms and the aryl portion is, for example, a phenyl group, these derivatives being, for instance, 4-tert-butyl-1-phenyl cyclohexanol;

callixarenes such as those mentioned in the book "Specialist Surfactants";

associations of 2,4,6-tri-aminopyrimidine substituted by an alkyl chain and dialkyl barbituric acid, the alkyl chains of which are linear or branched and comprise from 1 to 22 carbon atoms;

compounds such as those described in the document WO-A-01/07007, the disclosure of which is herein incorporated by reference, and having the following formula (V):

$$Q\text{-}O\text{—}W\text{—}(CHOH)_s\text{—}W^1\text{—}O\text{-}Q^1 \qquad (V)$$

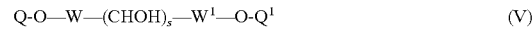

in which W and W', which may be identical or different, are chosen from —$CH_2$—, —CO— and in which Q and $Q^1$, which may be identical or different, are a hydrocarbon-based chain chosen from saturated or unsaturated linear or branched hydrocarbon-based chains containing at least 6 carbon atoms, and in which s is an integer from 2 to 4; such as the compounds in which W=$W^1$=—$CH_2$— and s=2 and the compounds in which W=$W^1$=—CO— and s=4;

gluconamide derivatives such as those disclosed in the article R. J. H HAFKAMP, Chem. Commun., (1997), pages 545-46 and in the article, J. org. Chem, vol 64, No.

2; 412-26 (1999), the disclosures of which are herein incorporated by reference and having a formula (VI):

    (VI)

in which $R^1$ is a hydrocarbon-based chain chosen from saturated or unsaturated linear, branched and cyclic hydrocarbon-based chains having 1 to 30 carbon atoms; this hydrocarbon-based chain optionally can comprise at least one hetero atom such as N, O and S; and for example the compounds in which $R_2$=—O—CO—$R_3$ or —O—$R_3$ with $R_3$ chosen from linear and branched alkyl chains containing 1 to 20 carbon atoms, $C_5$-$C_8$ cycloaliphatic and aromatic chains, $C_5$-$C_8$ heterocycles comprising N, O or S atoms, and for example the compounds in which $R_2$ is a $C_5$-$C_8$ saturated or unsaturated heterocycles comprising N, O, S atom such as $R_2$ is imidazolyl group; and cyclic ether derivatives of compound of formula VI, having the formula VI':

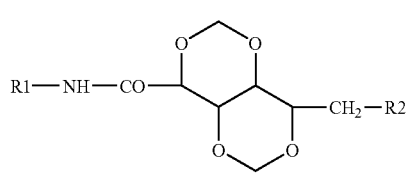    (VI')

wherein $R_1$ and $R_2$ has the same meaning as defined in formula (VI).

bis oxalylamides of aminoacides such as those mentioned in the article M. JOKIC, J. chem. soc., chem. commun., pages 1723-24 (1995), the disclosure of which is herein incorporated by reference, and for example having the formula VII:

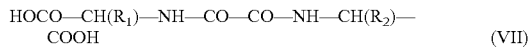    (VII)

in which $R_1$ and $R_2$ may be identical or different, are a group chosen from

—$CH_2$—$CH(CH_3)_2$; —$C_6H_5$; —$CH_2$—$C_6H_5$; —$CH(CH_3)_2$;

amide and urea derivatives of lysine ester such as those mentioned in the article K. HANABUSA, Chemistry Letters, p 1070-71 (2000), the disclosure of which is herein incorporated by reference, such as $N^\epsilon$-lauroyl-$N^\alpha$-stearyl aminocarbonyl-L-lysine (ethyl or methyl) ester and derivatives having a formula: $C_{11}$—$H_{23}$—CO—NH—$(CH_2)_4$—CH($COOR_1$)—NH—CO—$R_2$; in which $R_1$=—$CH_3$ or —$C_2H_5$ and $R_2$=—NH—$(CH_2)_{17}$—$CH_3$, —NH—$(CH_2)_n$—$CH_3$ derivatives from diamides benzene dicarboxylic of acides and valine such as those mentioned in the article K. HANABUSA, Chemistry Letters, 767-8 (1999), the disclosure of which is herein incorporated by reference, and for example:

in which -L-Val-represents: —NH—CH(CH($CH_3$)$_2$)—CO—;

monoalkyloxamides such as those disclosed by X. LUO, Chem. Commun., 2091-92, (2000), the disclosure of which is herein incorporated by reference, and for example having the formula:

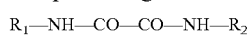

In which $R_1$ and $R_2$ which can be identical or different are a hydrocarbon-based chain chosen from saturated or unsaturated linear, branched and cyclic hydrocarbon-based chains having 1 to 30 carbon atoms;

bolaamphiphiles having 1-glucosamide head, such as N,N'-bis(β-D-glucopyranosyl) alcane-1, n-dicarboxamide, these compounds being mentioned in the article T. SHIMIZU, J. Am. Chem. Soc., 119, 2812-18 (1997), the disclosure of which is herein incorporated by reference, and has the formula VIII:

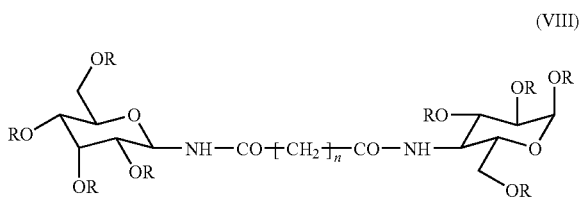    (VIII)

in which n is an integer from 2 to 30, R is —H or —CO—$R_1$ in which $R_1$ is a $C_1$-$C_{20}$ alkyl group,

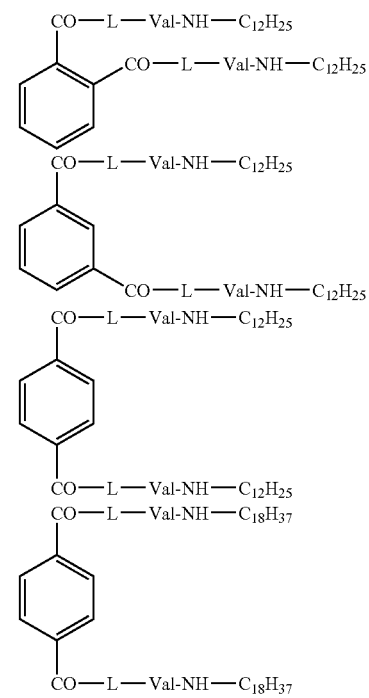

and for example the compound in which R=CO—$CH_3$ alkyl-2-ammonium-2-isobutylacetate p-toluene sulfonate such as those disclosed by K. HANABUSA, Colloïd Polym. Sci, 276, 252-59 (1998), the disclosure of which is herein incorporated by reference, and having the formula XII:

$p$—$CH_3$—$C_6H_4$—$SO_3^-$ $^+H_3N$—CH($R_1$)—CO—$OR_2$    (XII)

in which $R_1$=—$CH_2$—$CH(CH_3)_2$; —$CH(CH_3)_2$; —CH($CH_3$)—$CH_2$—$CH_3$; —$CH_2$—$C_6H_5CH_2$—$CH_2$—CO—O—$CH_2$—$(CH_2)_{10}$—$CH_3$ and $R_2$=—$CH_2$—$(CH_2)_n$—$CH_3$ with n an integer from 4 to 12.

cellobiose fatty esters, such a those mentioned in WO-A-00/61080, the disclosure of which is herein incorporated by reference, and WO-A-00/61081, the disclosure of which is herein incorporated by reference, and having the formula XIII:

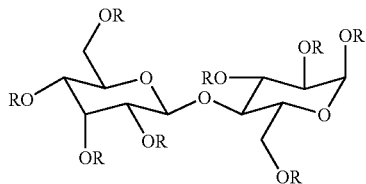
(XIII)

in which R=CO—R1 and R1=alkyl or alkylene group with 5 to 12 carbon atoms.

diamides having the formula XIV or XV

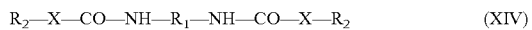
(XIV)

or

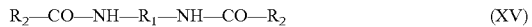
(XV)

in which $R_1$ is alkylene group chosen from $C_1$-$C_{50}$ linear, branched and cyclic groups and $C_5$-$C_8$ arylene groups and alkylen groups comprising $C_1$-$C_4$ alkyl group; and in which —X— represents —O— or —NH—; and in which $R_2$, which may be identical or different is a $C_8$-$C_{60}$ saturated or unsaturated linear or branched hydrocarbon-based chain, at least one $R_2$ comprising optionally a hydroxyl group or at least one hetero atom such as N, O, S or Si.

and mixtures thereof.

In one embodiment, amino acid amides such as N-acylamino acids and cyclohexane tricarboxamides, and mixtures thereof, are used.

Organogelator of Formula (II)

According to the invention, the organogelator may be a compound of formula (II) below:

in which:

R and R', which may be identical or different, are chosen from a hydrogen atom and hydrocarbon-based chains chosen from saturated linear, saturated branched, saturated cyclic, unsaturated linear, unsaturated branched and unsaturated cyclic hydrocarbon-based chains containing from 1 to 22 carbon atoms, for example from 6 to 18 carbon atoms, such as from 10 to 14 carbon atoms, optionally substituted with at least one group chosen from aryl (—$C_6H_5$), ester (—COOR" with R" being an alkyl group containing 2 to 12 carbon atoms), amide (—CONHR" with R" being an alkyl group containing from 2 to 12 carbon atoms), urethane (—OCONHR" with R" being an alkyl group containing from 2 to 12 carbon atoms) and urea NHCONHR" with R" being an alkyl group containing from 2 to 12 carbon atoms) groups; and/or optionally containing from 1 to 3 hetero atoms chosen from O, S and N; and/or optionally substituted with from 1 to 4 halogen atoms, in particular fluorine atoms, and/or with from 1 to 3 hydroxyl radicals, with the proviso that R and/or R' is other than hydrogen, and A is chosen from saturated and unsaturated, linear, cyclic and branched hydrocarbon-based chains containing from 1 to 18 carbon atoms, such as from 2 to 12 carbon atoms, and for example from 4 to 12 carbon atoms, optionally substituted with at least one group chosen from aryl (—$C_6H_5$), ester (—COOR" with R" being an alkyl group containing from 2 to 12 carbon atoms), amide (—CONHR" with R" being an alkyl group containing from 2 to 12 carbon atoms), urethane (—OCONHR" with R" being an alkyl group containing from 2 to 12 carbon atoms) and urea (—NHCONHR" with R" being an alkyl group containing from 2 to 12 carbon atoms) groups; and/or optionally containing from 1 to 3 hetero atoms chosen from O, S and N; and/or optionally substituted with from 1 to 4 halogen atoms, such as fluorine atoms, and/or with from 1 to 3 hydroxyl radicals.

According to formula (II), the expression "unsaturated hydrocarbon-based chain" means a chain which comprises at least one C=C double bond or at least one C≡C triple bond, it being possible for the chain also to be optionally substituted with at least one group chosen from aryl, ester, amide, urethane and urea groups; and/or optionally to comprise at least one hetero atom chosen from O, S and N; and/or optionally to be substituted with at least one fluorine atom and/or hydroxyl radical. The expression "hydrocarbon-based chain according to formula (II) comprising an oxygen, sulphur or nitrogen atom" includes, in particular, a hydrocarbon-based chain comprising a carbonyl (C=O), amine (—$NH_2$ or —NH—), thiol (—SH), thioether or ether group.

The compounds, for example, correspond to the formula (II) in which:

A is chosen from saturated and unsaturated but non-aromatic, optionally branched hydrocarbon-based rings containing from 4 to 12 carbon atoms, for example from 5 to 7 carbon atoms, optionally substituted with the substituents mentioned above and/or optionally comprising at least one hetero atom and/or optionally substituted with at least one halogen and/or hydroxyl radical;

R and R', which may be identical or different, are chosen from a hydrogen atom and hydrocarbon-based chains chosen from saturated linear, saturated branched, saturated cyclic, unsaturated linear, unsaturated branched and unsaturated cyclic hydrocarbon-based chains containing from 10 to 16 carbon atoms, for example, from 12 to 14 carbon atoms, such as a saturated, linear hydrocarbon-based chain; or A is a saturated hydrocarbon-based chain chosen from linear and branched saturated hydrocarbon-based chains containing from 2 to 18 carbon atoms, for example from 3 to 12 carbon atoms, optionally substituted with the substitutents mentioned above, and/or optionally comprising at least one hetero atom and/or optionally substituted with at least one halogen and/or hydroxyl radical;

R and R', which may be identical or different, are chosen from a hydrogen atom and a hydrocarbon-based chain chosen from saturated linear, saturated branched, saturated cyclic, unsaturated linear, unsaturated branched and unsaturated cyclic hydrocarbon-based chains, such as saturated, linear, hydrocarbon-based chains containing from 10 to 20 carbon atoms, for example, from 11 to 18 carbon atoms;

or alternatively

A is chosen from aryl and aralkyl rings containing from 4 to 12 carbon atoms, for instance from 5 to 8 carbon atoms, optionally substituted with the substituents mentioned above and/or optionally comprising at least one hetero atom and/or optionally substituted with at least one halogen and/or hydroxyl radical;

R and R', which may be identical or different, are chosen from a hydrogen atom and hydrocarbon-based chains chosen from saturated linear, saturated branched, saturated cyclic, unsaturated linear, unsaturated branched and unsaturated cyclic hydrocarbon-based chains, such as a saturated, linear, hydrocarbon-based chain, containing from 6 to 18 carbon atoms, for example from 10 to 16 carbon atoms.

The radical A may be, for example, a divalent radical such as cyclohexylene, ethylene, propylene, isopropylene, butylene, isobutylene, pentylene, hexylene, dodecylene, dodecanylene, benzylene, phenylene, methylphenylene, bis-phenylene or naphthalene.

The radicals R and R' may be chosen, independently of each other, from, for example, pentyl, hexyl, decyl, undecyl, dodecyl, pentadecyl, hexadecyl, heptadecyl, octadecyl, 3-dodecyloxypropionyl, 3-octadecyloxy-propionyl, 3-dodecyloxypentyl, 3-octadecyloxypentyl and 11-hydroxyheptadecyl radicals. In one embodiment R and R' are identical.

When the radical A is cyclic, the radicals R—CO—NH— and R'—CO—NH— may be in an ortho, meta or para position. Moreover, they may be in a cis or trans position relative to each other. In one embodiment, the compounds of formula (II) is a mixture of cis and trans compounds.

The compounds of formula (II) may be chosen from the compounds corresponding to one of the following formulae:

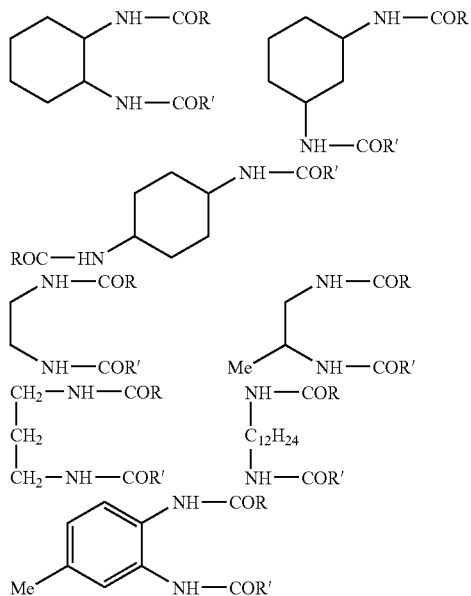

in which R and R' have the same meanings as above.

Among the compounds which may be used as organogelators in the composition of the invention, mention may be made of:

N,N'-bis(dodecanoyl)-1,2-diaminocyclohexane, in particular in trans form (compound of formula (II) with R=R'=n-C$_{11}$H$_{23}$ and A=1,2-cyclohexylene divalent radical, also known as (2-dodecanoylaminocyclohexyl) dodecanamide. This compound is described in particular in Hanabusa, K; Angew. Chem., 108, 1997, 17, pages 2086-2088, N,N'-bis(dodecanoyl)-1,3-diaminocyclohexane, in particular in trans form (compound of formula (II) with R=R'=n-C$_{11}$H$_{23}$ and A=1,3-cyclohexylene divalent radical, also known as (3-dodecanoylaminocyclohexyl-dodecanamide), N,N'-bis(dodecanoyl)-1,4-diaminocyclohexane, in particular in trans form (compound of formula (II) with R=n-C$_{11}$H$_{23}$ and A=1,4-cyclohexylene divalent radical, also known as (4-dodecanoylaminocyclohexyl) dodecanamide), N,N'-bis(dodecanoyl)-1,2-ethylenediamine (compound of formula (II) with R=R'=n-C$_{11}$H$_{23}$ and A=1,2-ethylene divalent radical, also known as (2-dodecanoylaminoethyl)dodecanamide), N,N'-bis(dodecanoyl)-1-methyl-1,2-ethylenediamine (compound of formula (II) with R=R'=n-C$_{11}$H$_{23}$ and A=1-methyl-1,2-ethylene divalent radical, also known as (2-dodecanoylamino-2-methylethyl) dodecanamide), N,N'-bis(dodecanoyl)-1,3-diaminopropane (compound of formula (II) with R=R'=n-C$_{11}$H$_{23}$ and A=1,3-propylene divalent radical, also known as (2-dodecanoylamino-propyl) dodecanamide), N,N'-bis(dodecanoyl)-1,12-diaminododecane (compound of formula (II) with R=R'=n-C$_{11}$H$_{23}$ and A=1,12-dodecylene divalent radical, also known as (2-dodecanoylaminododecyl) dodecanamide), N,N'-bis(dodecanoyl)-3,4-diaminotoluene (compound of formula (II) with R=R'=n-C$_{11}$H$_{23}$ and A=1-methyl-3,4-phenylene divalent radical, also known as (2-dodecanoylamino-4-methylphenyl) dodecanamide).

The compounds of formula (II) can be prepared according to processes that are well known to those skilled in the art.

In particular, they may be obtained by reacting a diamine H$_2$N-A-NH$_2$ with an acid chloride RCOCl and/or R'COCl with R and R' having the above meaning, but other than a hydrogen atom, in an organic solvent medium which is compatible for carrying out the reaction (1 mol of acid chloride is used per 1 mol of diamine if it is desired to obtain a compound of formula (I) containing only one group R other than a hydrogen atom, or 2 mol of acid chloride RCOCl and/or R'COCl if it is desired to obtain a compound of formula (II) with R and R' other than a hydrogen atom). The reaction is preferably carried out in the presence of a base capable of neutralizing the formation of the HCl released during the reaction. The diamide formed is extracted from the reaction medium according to the conventional extraction techniques that are well known to those skilled in the art.

The compounds of formula (II) can be prepared according to processes that are well known to those skilled in the art and can be used, alone or as a mixture, in the composition of the invention.

Standard Preparation of the Compounds of Formula (II) for R=R'

The diamine and two equivalents of triethylamine are dissolved in 50 ml of tetrahydrofuran. Two equivalents of acyl chloride dissolved in THF are added and the reaction mixture is heated to the reflux point of the tetrahydrofuran, while monitoring the disappearance of the acyl chloride by infrared spectroscopy (most typically, two hours). The solution is filtered from the precipitate, the organic phase is concentrated and a liquid/liquid extraction is performed on the solid compound obtained. The organic phase is subsequently dried and then concentrated, and the solid product obtained is recrystallized.

Organogelator of Formula (III)

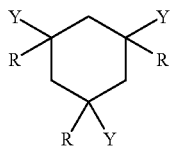

in which:
R is identical or different and each is chosen from a hydrogen atom, a saturated linear hydrocarbon-based chain, and a saturated branched hydrocarbon-based chain, wherein said hydrocarbon-based chains contain from 1 to 6 carbon atoms, for example from 1 to 4 carbon atoms;
Y is identical or different and each is a group chosen from the following groups: —CO—S—R'; —CO—NHR'; —NH—COR' and —S—COR'; in which R' is identical or different and each is chosen from:
a hydrogen atom;
an aryl group;
an aralkyl group, i.e., an aryl group substituted with a hydrocarbon-based chain chosen from saturated, linear hydrocarbon-based chains and saturated, branched hydrocarbon-based chains, wherein the hydrocarbon based chain contains from 1 to 22 carbon atoms, for example from 10 to 18 carbon atoms; and
a saturated hydrocarbon-based chain chosen from linear, branched and cyclic hydrocarbon-based chains containing from 1 to 22 carbon atoms, for example from 10 to 18 carbon atoms, optionally substituted with at least one group chosen from aryl, ester, amide and urethane groups; and/or optionally comprising at least one hetero atom chosen from O, S and N; and/or optionally substituted with at least one fluorine atom and/or hydroxyl radical.
R, for example, is chosen from a hydrogen atom.
Y, for example, is chosen from the groups —CO—NHR' and —NH—COR'.
R', for example, is chosen from an aryl group; an aralkyl group in which the linear or branched alkyl chain contains from 12-16 carbon atoms; and a linear or branched $C_{11}$-$C_{18}$ alkyl chain.
In one embodiment, Y is chosen from a group —CO—NHR' in which R' is chosen from an aryl group substituted with a $C_{12}$-$C_{16}$ alkyl chain chosen from linear and branched $C_{11}$-$C_{16}$ alkyl chains; or R' is chosen from an unsubstituted linear $C_{11}$-$C_{18}$ alkyl chain and an unsubstituted branched $C_{11}$-$C_{18}$ alkyl chain.
The three substitutents represented by Y can be, in the compounds of formula (III), in cis-cis, cis-trans or trans-trans conformation relative to each other. In particular, at least one of these substituents may be placed in an equatorial position on the cyclohexane ring; for example, all the substituents Y are placed in an equatorial position. In one embodiment, the compounds of formula (III) is a mixture of cis-cis, cis-trans and/or trans-trans compounds.
Among the compounds of formula (III) which can be used as an organogelator, alone or as a mixture, in the composition of the invention, mention may be made of:
cis-1,3,5-tris(dodecylaminocarbonyl)cyclohexane,
cis-1,3,5-tris(octadecylaminocarbonyl)cyclohexane,
cis-1,3,5-tris[N-(3,7-dimethyloctyl)-aminocarbonyl]cyclohexane,
trans-1,3,5-trimethyl-1,3,5-tris(dodecylaminocarbonyl)cyclohexane, and
trans-1,3,5-trimethyl-1,3,5-tris(octadecylaminocarbonyl)cyclohexane.

The compounds of formula (III) are well known to those skilled in the art and can be prepared according to the usual processes.

It is also possible to add to the composition an organic compound as set forth in U.S. Pat. No. 6,156,325, the disclosure of which is incorporated by reference herein. Such compounds include urea urethanes having the following formula:

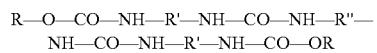

wherein R represents $C_nH_{2n+1}$— or $C_mH_{2m+1}(C_pH_{2p}O)_r$—; n represents an integer having a value of from 4 to 22; m represents an integer having a value of from 1 to 18; p represents an integer having a value of from 2 to 4; and r represents an integer having a value of from 1 to 10,
R' represents:

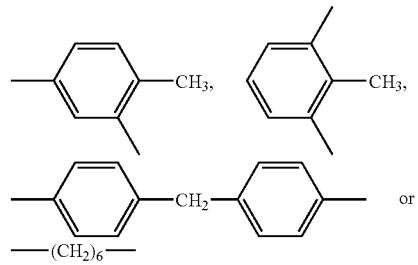

and R" represents:

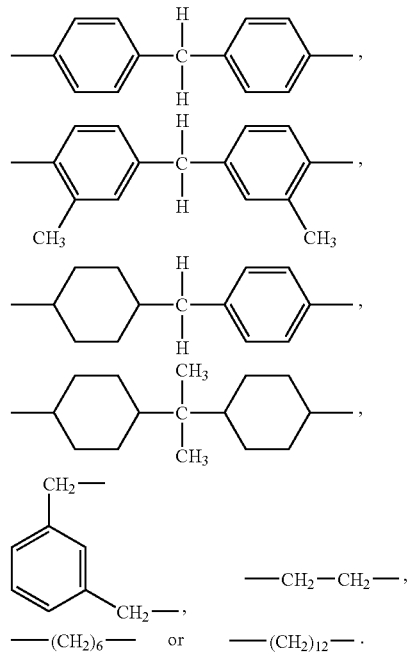

As is evident from the urea urethane formula above, the alkyl groups and alkyl portions designated for the R variable are saturated.

Organogelator of Formula (IV)

According to the invention the organogelator may be at least one organogelator of formula (IV);

RNHCONHANHCONHR wherein A and R have the same definition as the one provided above for formula (II), expressed most broadly as:

R, which may be identical or different, is each chosen from a hydrogen atom and hydrocarbon-based chains chosen from saturated linear, saturated branched, saturated cyclic, unsaturated linear, unsaturated branched and unsaturated cyclic hydrocarbon-based chains containing from 1 to 22 carbon atoms, for example from 6 to 18 carbon atoms, optionally substituted with at least one group chosen from aryl (—C$_6$H$_5$), ester (—COOR" with R" being an alkyl group containing from 2 to 12 carbon atoms), amide (—CONHR" with R" being an alkyl group containing from 2 to 12 carbon atoms), urethane (—OCONHR" with R" being an alkyl group containing from 2 to 12 carbon atoms) and urea (—NHCONHR" with R" being an alkyl group containing from 2 to 12 carbon atoms) groups; and/or optionally containing from 1 to 3 hetero atoms chosen from O, S and N; and/or optionally substituted with from 1 to 4 halogen atoms, in particular fluorine atoms, and/or with from 1 to 3 hydroxyl radicals, with the proviso that at least one R is other than hydrogen, and A is chosen from saturated and unsaturated, linear, cyclic and branched hydrocarbon-based chains containing from 1 to 18 carbon atoms, such as from 2 to 12 carbon atoms, optionally substituted with at least one group chosen from aryl (—C$_6$H$_5$), ester (—COOR" with R" being an alkyl group containing from 2 to 12 carbon atoms), amide (—CONHR" with R" being an alkyl group containing from 2 to 12 carbon atoms), urethane (—OCONHR" with R" being an alkyl group containing from 2 to 12 carbon atoms) and urea (—NHCONHR" with R" being an alkyl group containing from 2 to 12 carbon atoms) groups; and/or optionally containing from 1 to 3 hetero atoms chosen from O, S and N; and/or optionally substituted with from 1 to 4 halogen atoms, such as fluorine atoms, and/or with from 1 to 3 hydroxyl radicals.

In one embodiment, the inventive composition contains from 0.1% to 80% by weight of organogelator. In another embodiment, the composition contains from 0.5% to 60% by weight of organogelator, for example, from 1% to 40% or from 2% to 30%, including all values and ranges there between.

Active Agents

The composition of the present invention advantageously contains at least one cosmetic active agent and/or at least one dermatological active agent, i.e., an agent having a beneficial effect on the skin, lips or body growths and/or at least one coloring agent.

Gelling Agent

The composition of the invention may also contain at least one agent useful for gelling a liquid fatty phase. The gelling agent increases the liquid fatty phase viscosity and leads to a solid or flowable composition when introduced in said fatty phase. The gelling agent does not encompass waxes, in the sense that it is not waxy.

The at least one gelling agent may be chosen from gelling agents in polymeric form and gelling agents in mineral form.

In one embodiment, the at least one gelling agent is not soluble in an aqueous phase or in water.

The gelling agent according to the present invention is preferably selected from the group consisting of agents that gel via chemical reticulation and agents that gel via physical reticulation.

Gelling Agents that Gel Via Chemical Reticulation

According to one embodiment, crosslinked elastomeric polyorganosiloxanes of three-dimensional structure are preferred. These elastomeric silicones can bear hydrophile groups, such as polyoxyethylene or copoly(oxyethylene/oxypropylene).

As elastomeric polyorganosiloxanes which can be used in the invention, mention may be made of the crosslinked elastomeric polyorganosiloxanes described in application EP-A-0,295,886, the disclosure of which is incorporated herein by reference. According to that application, they are obtained by addition reaction and crosslinking, in the presence of a platinum-type catalyst, of at least:

a polyorganosiloxane having at least two C$_2$ to C$_6$ lower alkenyl groups per molecule; and a polyorganosiloxane having at least two hydrogen atoms linked to a silicon atom per molecule. It is also possible to use the polyorganosiloxanes described in U.S. Pat. No. 5,266,321, the disclosure of which is incorporated by reference herein. According to that patent, they are chosen in particular from:

polyorganosiloxanes comprising R$_2$SiO and RSiO$_{1.5}$ units and optionally R$_3$SiO$_{0.5}$ and/or SiO$_2$ units in which the radicals R, independently of each other, are chosen from a hydrogen, an alkyl such as methyl, ethyl or propyl, an aryl such as phenyl or tolyl, an unsaturated aliphatic group such as vinyl, the weight ratio of the units R$_2$SiO to the units RSiO$_{1.5}$ ranging from 1/1 to 30/1;

polyorganosiloxanes which are insoluble and swellable in silicone oil, obtained by addition of an polyorganohydrogenosiloxane (1) and of a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic. Optionally, these polyorganosiloxanes can comprise from 1 to 40 oxyalkylene groups, such as oxypropylene and/or oxyethylene groups.

As examples of elastomeric polyorganosiloxanes which can be used according to the invention, mention may be made of those sold or made under the names KSG6 from Shin-Etsu, Trefil E-505C or Trefil E-506C from Dow-Corning, Gransil from Grant Industries (SR-CYC, SR DMF10, SR-DC556) or those marketed in the form of preconstituted gels (KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric or emulsifying elastomers such as those sold under the names of KSG-210, KSG-30, KSG-31, KSG-32, KSG-33, KSG-40, KSG 41, KSG-42, KSG43 and KSG-44 from Shin-Etsu. A mixture of these commercial products may also be used.

Gelling Agents that Gel Via Physical Reticulation

Gelling agents that gel via physical reticulation, in particular via molecular muddling, hydrogen interactions, sequences incompatibility or dipolar interactions, as well as liposoluble polymers having liquid crystal groups, are preferred.

Gelling agents that gel via molecular muddling are polymers having high molecular weights, preferably higher than 500 000, such as silicone gums.

The silicone gum can correspond to the formula:

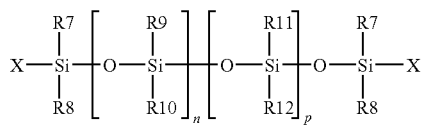

in which:

$R_7$, $R_8$, $R_{11}$ and $R_{12}$ are identical or different, and each is chosen from alkyl radicals comprising from 1 to 6 carbon atoms, $R_9$ and $R_{10}$ are identical or different, and each is chosen from alkyl radicals comprising from 1 to 6 carbon atoms and aryl radicals, X is chosen from alkyl radicals comprising from 1 to 6 carbon atoms, a hydroxyl radical and a vinyl radical, n and p are chosen so as to give the silicone gum a viscosity of greater than 100 000 mPa·s, such as greater than 500 000 mPa·s.

In general, n and p can each take values ranging from 0 to 5 000, such as from 0 to 3 000.

Among the silicone gums which can be used according to the invention, mention may be made of those for which:

the substituents $R_7$ to $R_{12}$ and X represent a methyl group, p=0 and n=2 700, such as the product sold or made under the name SE30 by the company General Electric, the substituents $R_7$ to $R_{12}$ and X represent a methyl group, p=0 and n=2 300, such as the product sold or made under the name AK 500 000 by the company Wacker, the substituents $R_7$ to $R_{12}$ represent a methyl group, the substituent X represents a hydroxyl group, p=0 and n=2 700, as a 13% solution in cyclopentasiloxane, such as the product sold or made under the name Q2-1401 by the company Dow Corning, the substituents $R_7$ to $R_{12}$ represent a methyl group, the substituent X represents a hydroxyl group, p=0 and n=2 700, as a 13% solution in polydimethylsiloxane, such as the product sold or made under the name Q2-1403 by the company Dow Corning, and the substituents $R_7$, $R_8$, $R_{11}$, $R_{12}$ and X represent a methyl group and the substituents $R_9$ and $R_{10}$ represent an aryl group, such that the molecular weight of the gum is about 600 000, for instance the product sold or made under the name 761 by the company Rhone-Poulenc (Rhodia Chimie).

In preferred embodiments, the silicone gum correspond to the following formula:

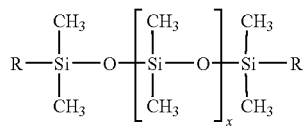

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cycohexyl, phenyl, fluoroalkyl, and mixtures thereof. The silicone gums employed in the present invention may be terminated by triorganosilyl groups of the formula $R'_3$ where R' is a radical of monovalent hydrocarbons containing from 1 to 6 carbon atoms, hydroxyl groups, alkoxyl groups and mixtures thereof. The silicone gums used in the invention have an affinity with the structuring polymer and/or with the silicone gum, and the liquid fatty phase, the polymer and the silicone gum form a physiologically acceptable medium.

A particularly preferred fluid diorganopolysiloxane polymer is poly(dimethylsiloxane), herein referred to as PDMS. Also useful is a mixture of silicone gums such as the commercially available DC 1503 which is a blend of dimethicone and dimethiconol. Other useful silicone gums are DC 1428 fluid (Dow Corning) and those silicone gums described in U.S. Pat. No. 4,574,082, the contents of which are incorporated herein by reference.

In certain embodiments of the present invention, crystalline silicone compounds are included in the compositions.

A crystalline silicone compound is a compound comprising silicone in its molecule, which is solid at room temperature, and has a crystalline character. This compound or class of compounds is compatible with the liquid fatty phase and the structuring agent.

The crystalline silicone compounds belong to a class of alkyl siloxane waxes corresponding to the formulae below:

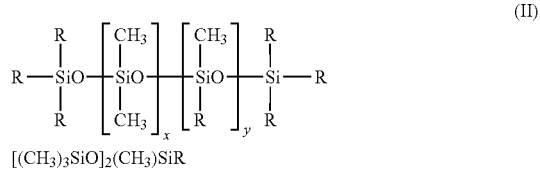

[(CH₃)₃SiO]₂(CH₃)SiR (CH₃)₃SiO[(CH₃)₂SiO]ₓ(RCH₃SiO)ᵧSi(CH₃)₃

This could also be written as $R_3SiO[(CH_3)_2SiO]_x(RCH_3SiO)_ySiR_3$ where R is an alkyl chain. x may be 0. The substituent R may be as low as 1 or as high as 50 or more as long as this silicone compound crystallizes at room temperature.

Examples of crystalline silicone compounds include, but are not limited to, C20-24 Alkyl Methicone, C24-28 Alkyl Dimethicone, C20-24 Alkyl Dimethicone, C24-28 Alkyl Dimethicone commercially available from Archimica Fine Chemicals, Gainesville, Fla. under the designation of SilCare 41 M40, SilCare 41 M50, SilCare 41 M70 and SilCare 41 M80. Stearyl Dimethicone available as SilCare 41 M65 from Archimica or as DC-2503 from Dow-Corning, Midland, Mich. Similarly, stearoxytrimethylsilane sold as SilCare 1 M71 or DC-580 may be used in an embodiment of this invention. Furthermore, similar crystalline compounds are available from Degussa Care Specialties, Hopewell, Va. under the designation ABIL Wax 9810, 9800, or 2440, or Wacker-Chemie GmbH, Burghausen, Germany, under the designation BelSil SDM 5055, or OSi Specialties, Greenwich, Conn. under the designation Silsoft. Other crystalline silicone compounds include C30-45 Alkyl Methicone available from Dow Corning as AMS-C30 Wax, as well as GE's SF1642, or SF-1632 available from General Electric, Fairfield, Conn.

Gelling agents that gel the liquid fatty phase via hydrogen interactions are preferably chosen in the group consisting of:

amino silicones polymers having triazinyl groups or pyrimidinyl groups bound to amino groups of amino silicones as described in patent application EP 0 751 170, the disclosure of which is incorporated herein by reference, non-silicone polyamides, ends of which bear ester or triamides functions, such as compounds described in patents and patent applications U.S. Pat. No. 5,783,657, U.S. Pat. No. 6,268,466, WO 01/95871, WO 00/40216, U.S. 2002/0035237, and EP 1 068 856, the disclosure of which are incorporated herein by reference, polyurethanes, such as compounds described in patent applications DE 10022247 and FR 2 814 365, the disclosure of which are incorporated herein by reference, and vinyl and/or (meth)acrylic polymers bearing lateral groups that can create mutual hydrogen interactions, such as compounds described in patent application WO 93/01797, the disclosure of which is incorporated herein by reference.

Gelling agents that gel the liquid fatty phase via sequences incompatibility are preferably selected from the group consisting of:

block (di ou tri blocks) copolymers, such as polystyrene-silicone, or polyethylene-silicone, described in patents U.S. Pat. No. 6,225,390, U.S. Pat. No. 6,160,054, U.S. Pat. No. 6,174,968 and U.S. Pat. No. 6,225,390, the disclosures of which are incorporated herein by reference, block or grafted copolymers comprising a silicone sequence and another sequence or graft that is polyvinyl or poly(meth)acrylic, such as those described in patents U.S. Pat. No. 5,468,477 et U.S. Pat. No. 5,725,882, the disclosures of which are incorporated herein by reference.

polymers or copolymers resulting from the polymerization or copolymerization of an ethylenic monomer, comprising one or more ethylenic, preferably conjugated, bonds (or dienes), polymers or copolymers resulting from the polymerization or copolymerization of an ethylenic monomer, in particular use may be made of vinyl, acrylic or methacrylic copolymers which may be block copolymers, such as diblock or triblock copolymers, or even multiblock or starburst or radial copolymers. The at least one ethylenic gelling agent may comprise, for example, a styrene block (S), an alkylstyrene block (AS), an ethylene/butylene block (EB), an ethylene/propylene block (EP), a butadiene block (B), an isoprene block (I), an acrylate block (A), a methacrylate block (MA) or a combination of these blocks.

In one embodiment, a copolymer comprising at least one styrene block is used as gelling agent or ethylenic rheological agent. A triblock copolymer and in particular those of the polystyrene/polyisoprene or polystyrene/polybutadiene type, such as those sold or made under the name "Luvitol HSB" by BASF and those of the polystyrene/copoly(ethylene-propylene) type or alternatively of the polystyrene/copoly(ethylene/butylene) type, such as those sold or made under the brand name "Kraton" by Shell Chemical Co. or Gelled Permethyl 99A by Penreco, may be used. Styrene-methacrylate copolymers can also be used.

As ethylenical gelling agent which can be used in the composition of the invention, mention may be made, for example, of Kraton (G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton G1750X (EP) multiarm, Kraton G1765X (EP) multiarm, Kraton D-1101 (SBS), Kraton D-1102 (SBS), Kraton D-1107 (SIS), Gelled Permethyl 99A-750, Gelled Permethyl 99A-753-58 (mixture of starburst block polymer and triblock polymer), Gelled Permethyl 99A-753-59 (mixture of starburst block polymer and triblock polymer), Versagel 5970 and Versagel 5960 from Penreco (mixture of starburst polymer and triblock polymer in isododecane), and OS 129880, OS 129881 and OS 84383 from Lubrizol (styrene-methacrylate copolymer).

Di or triblocks such as polystyrene-copoly(ethylene/propylene) or polystyrene-copoly(ethylene/butylene) such as those described in patent applications WO 98/38981 and U.S. 2002/0055562, the disclosures of which are hereby incorporated by reference, are also included in the present invention.

Gelling agents that gel via dipolar interactions are preferably chosen from compounds describes in documents WO 01/30886 et U.S. Pat. No. 6,228,967, the disclosures of which are incorporated herein by reference. Ionized groups of said compounds, for example zwitterionic groups, create said dipolar interactions.

Gelling agents such as liposoluble polymers having liquid crystal groups are also preferred according to the present invention, especially liposoluble polymers whose backbone is silicone, vinyl and/or (meth)acrylic and that possess des lateral liquid crystal groups, in particular compounds described in patent application FR 2 816 503, the disclosure of which is incorporated herein by reference.

In another embodiment, the at least one gelling agent may be in mineral form with particle sizes that cause little or no light scattering. Thus, it may be possible to obtain a translucent or even transparent composition.

As modified clays which can be used, mention may be made of hectorites modified with an ammonium chloride of a $C_{10}$ to $C_{22}$ fatty acid, such as hectorite modified with distearyidimethylammonium chloride, also known as quatermium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyidimethylbenzoylammonium chloride, known as steralkonium bentonites, such as the products sold or made under the names Claytone APA and Claytone AF by the company Southern Clay, and Baragel 24 sold or made by the company Rheox.

As other mineral gelling agents, which can be used in the invention, mention may be made of silica, such as fumed silica. The fumed silica may have a particle size, which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be:

trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot;

groups derived from reacting fumed silica with silane alkoxides or siloxanes. These treated silicas are, for example, the products sold or made under the reference "Aerosil R805®" by the company Degussa.

According to the invention, hydrophobic silica, such as fumed silica, may be used as lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one liposoluble gelling agent can allow the exudation of the composition to be limited and can allow its stability to be increased, while at the same time conserving the composition's glossy appearance, which is not possible with waxes such as those used conventionally in cosmetics and dermatology. These gelling agents can be used, for example, at concentrations of from 0.05% to 35% relative to the total weight of the composition, for example from 0.5% to 20% or from 1% to 10%.

In addition, short chain esters may be included in the compositions of the present invention.

According to the invention, the esters may either be monoesters, diesters or polyesters. These esters may be linear, branched or cyclic, saturated or unsaturated. These esters should preferably be branched and saturated. They may also be aliphatic or aromatic.

These esters may have from 6 to 25 carbon atoms and particularly from 14 to 22 carbon atoms. They may be chosen amongst acid esters having from 2 to 18 carbon atoms, and particularly amongst alcohol esters having from 2 to 20 carbon atoms or amongst polyols having from 2 to 8 carbon atoms or their mixtures, on condition that the number of carbon atoms is higher than 10, so that the ester is not volatile and penetrates the skin.

Particularly, these esters are hydrocarbon-based esters which correspond to the following formula RCOOR' where R represents a residue of fatty acid having from 1 to 29 carbon atoms, and R' represents a hydrocarbon-based chain containing from 2 to 30 carbon atoms, on condition that the number of carbon atoms in R' is higher than 10, so that the ester is not volatile and penetrates the skin.

The ester may be chosen among a non-limitative list including the following:

Neopentanoic acid esters such as isodecyl neopentanoate, isotridecyl neopentanoate, isostearyl neopentanoate, octyldocecyl neopentanoate, Isononanoic acid esters such as isononyl isononanoate, octyl isononanoate, isodecyl isononanoate, isotridecyl isononanoate, isostearyl isononanoate, ethylhexyl isononanoate, Isopropylic alcohol esters, such as isopropyl myristate, isopropyl palmitate, isopropyl stearate or isostearate, isopropyl laurate, diisopropyl adipate, Alkyl or polyalkyl octanoates, decanoates or ricinoleates, such as cetyl octanoate, tridecyl octanoate, Polyalkylene glycol esters, such as polyethylene glycol diheptanoate, hexanoate-2-diethyl propylene glycol and their mixtures, Benzoate alkyls particularly benzoate alkyls having from 12 to 15 carbon atoms, Hydroxylated esters such as isostearyl lactate and diisostearyl malate, and Pentaerythritol esters.

Examples of short chain esters also include purcellin oil (cetostearyl octanoate), ethylhexyl ethylhexanoate, dicapryl ester, 2-ethylhexyl palmitate, 2-ethyl-palmitate and isostearyl isostearate.

The isononyl isononanoate and diisostearyl malate are particularly suited for the embodiment of this invention.

This or these hydrocarbon-based ester(s) may be used in the composition at a percentage of 5 to 90%, notably of 10 to 60%, particularly of 20 to 50% by weight of the total weight of the composition.

Additional ingredients which offer similar cosmetic properties as the short chain esters are short chain ethers which may be represented as

J—O—K where J and K are identical or different and represent a linear or branched alkyl radical from 1 to 40 carbon atoms, preferably from 7 to 19 carbon atoms, possibly including one or more double bonds. An example of such an ether includes dicapryl ether.

Waxes

The composition can optionally contain one or more waxes to improve the structuring in stick form, although this rigid form can be obtained in the absence of wax. For the purposes of the present invention, a wax is a lipophilic fatty compound that is solid at room temperature (25° C.) and atmospheric pressure (760 mmHg, i.e. 101 KPa), which undergoes a reversible solid/liquid change of state, having a melting point of greater than 40° C. and further such as greater than 55° C. and which may be up to 200° C., and having an anisotropic crystal organization in the solid state. The size of the crystals is such that the crystals diffract and/or scatter light, giving the composition a cloudy, more or less opaque appearance. By bringing the wax to its melting point, it is possible to make it miscible with oils and to form a microscopically homogeneous mixture, but on returning the temperature of the mixture to room temperature, recrystallization of the wax in the oils of the mixture is obtained. It is this recrystallization in the mixture which is responsible for the reduction in the gloss of the mixture. Thus, the composition advantageously contains little or no wax, and in particular less than 5% wax.

For the purposes of the invention, the waxes are those generally used in cosmetics and dermatology; they are, for example, of natural origin, for instance beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C.

According to the invention, the melting point values correspond to the melting peak measured by the "Differential Scanning Calorimetry" method with a temperature rise of 5 or 10° C./min.

Liposoluble or Dispersible Polymers

The composition of the invention also can contain at least one polymer that is liposoluble or dispersible in the medium, may have film-forming properties, and may have, for example, an average molecular weight of from 500 to 1,000,000, such as from 1,000 to 500,000, and for example, further such as from 5,000 to 100,000, and even further such as from 5,000 to 20,000. This at least one liposoluble polymer may contribute towards increasing the viscosity and/or improving the staying power of the film. The at least one liposoluble polymer can have a softening point of not more than 30° C.

As examples of liposoluble polymers which can be used in the invention, mention may be made of: polyalkylenes, in particular polybutene, poly(meth)acrylates, alkylcelluloses with a linear or branched, saturated or unsaturated $C_1$ to $C_8$ alkyl radical, such as ethylcellulose and propylcellulose, silicone polymers that are compatible with the fatty phase, as well as vinylpyrrolidone (VP) copolymers, and mixtures thereof.

Vinylpyrrolidone copolymers, copolymers of a $C_2$ to $C_{30}$, such as $C_3$ to $C_{22}$ alkene, and combinations thereof, can be used. As examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

Not only for the staying power properties but also for the feel and consistency properties of the film, the PVP/hexadecene copolymer having an average molecular weight of from 7,000 to 7,500 or alternatively the PVP/eicosene copolymer having an average molecular weight of from 8,000 to 9,000 can be used.

The liposoluble or dispersible polymers in the composition of the invention can be also used in an amount of from 0.01% to 20% (as active material) relative to the total weight of the composition, such as, for example, from 1% to 10%, if they are present.

Emollients

Emollients and/or humectants that may be used in the compositions of the invention include glycerin, propylene glycol, and emollients and other similar ingredients disclosed in the *International Cosmetic Ingredient Dictionary and Handbook Vol. 4* ($9^{th}$ ed. 2002), more particularly the emollients disclosed on pages 2930-2936. The disclosure of the *International Cosmetic Ingredient Dictionary and Handbook Vol. 4*, pages 2930-2936, is hereby incorporated by reference.

Surfactants

The compositions of the invention may further include formulation aids which are usually employed in the field of application envisaged. The formulation aids used in the present invention can be, but are not limited to, surfactants. Useful surfactants include, but are not limited to, organic and organosilicone emulsifiers for water-in-oil systems. Examples of organic emulsifiers include any ethoxylated surfactants known in the art such as Polysorbate-20, Laureth-7, Laureth-4, Sepigel® 305 available from SEPPIC and other similar ingredients disclosed in the *International Cosmetic Ingredient Dictionary and Handbook Vol. 4* ($9^{th}$ ed. 2002), more particularly the emulsifiers disclosed on pages 2962-2971. The disclosure of the *International Cosmetic Ingredient Dictionary and Handbook Vol. 4*, pages 2962-2971, is hereby incorporated by reference. Examples of organosilicone emulsifiers include cetyl dimethicone copolyol-polyglyceryl-4-isostearate-hexylaurate (ABIL® WE 09) available from Goldschmidt Chemical Corporation, Cetyl Dimethicone Copolyol (ABIL® EM 90), (ABIL® EM 97), Laurylmethicone Copolyol (5200), Cyclomethicone (and) Dimethicone Copolyol (DC 5225 C and DC 3225 C) available from GE Silicones, Cyclopentasiloxane & Dimethicone Copolyol (GE SF 1528) or any other formulation aids known by one of skill in the art.

Plasticizers

Plasticizers may also be added to the compositions to improve the flexibility and cosmetic properties of the resulting formulation. Plasticizers are materials which soften synthetic polymers. They are frequently required to avoid brittleness and cracking of film formers/resins. One skilled in the art may routinely vary the amount of plasticizer desired based on the properties desired and the application envisaged. Plasticizers useful in the practice of the invention include lecithin, polysorbates, dimethicone copolyol, glycols, citrate esters, glycerin, dimethicone, and other similar ingredients disclosed in the *International Cosmetic Ingredient Dictionary and Handbook Vol. 4* ($9^{th}$ ed. 2002), more particularly the plasticizers disclosed on page 2927. The disclosure of the International Cosmetic Ingredient Dictionary and Handbook Vol. 4, page 2927, is hereby incorporated by reference.

Sunscreens

In one embodiment, the composition may contain sunscreens. In certain embodiments, the combination of the polysiloxane-containing polymer when combined with one or more sunscreens improves, quite significantly, the overall SPF value of the composition relative to a composition without the polysiloxane-containing polymer.

Sunscreens may be inorganic nanoparticles or organic compounds. In one embodiment the nanoparticles are inorganic compounds composed essentially of metal oxides. Suitable metal oxides comprise one or more of iron oxide, aluminum oxide, zirconium oxide, vanadium oxide, niobium oxide, tantalum oxide, chromium oxide, molybdenum oxide, tungsten oxide, cobalt oxide, nickel oxide, cerium cupric oxide, zinc oxide, tin oxide, antimony oxide titanium dioxide and mixtures thereof, among others. In yet another embodiment titanium dioxide and zinc oxide are used. Without being limited to theory, in most cases the metal oxide nanoparticles provide a sun protection benefit by diffracting the ultraviolet light. The elemental size of 1 nanoparticle is typically from less than 1 μm in size, including from about 100 nm to about 500 nm, including about 200 nm to about 350 nm.

Sunscreens according to this invention which are chemical absorbers actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties which are discussed at length in "Sunscreens—Development, Evaluation and Regulatory Aspects," by N. Shaath et al., 2nd. Edition, pages 269-273, Marcel Dekker, Inc. (1997). This discussion, in its entirety, is incorporated by reference herein.

The sunscreens which may be formulated according to the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes, diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517,104, EP-0,570,838, EP-0,796,851, EP-0,775,698, EP-0,878,469, EP-0,933,376, EP-0,893,119, EP-0,669,323, GB-2,303,549, DE-1,972,184 and WO-93/04665, also expressly incorporated by reference.

A wide variety of sunscreens is described in U.S. Pat. No. 5,087,445, issued to Haffey et al. on Feb. 11, 1992; U.S. Pat. No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

Non-limiting examples of sunscreens which may be formulated into the compositions of the instant invention include those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N, N-trimethyl-4-(2-oxoborn-3-ylidene methyl)anillinium methyl sulfate, and mixtures thereof.

Sunscreens active in the UV-A and/or UV-B range can also include:
p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate,
3-(4'-trimethylammunium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone,
2-hydroxy-4-n-octoxybenzophenone,
2-hydroxy-4-methoxy-4'-methoxybenzophenone,
-(2-oxoborn-3-ylidene)-tolyl-4-sulfonic acid and soluble salts thereof,
-(4'-sulfo)benzyliden-bornan-2-one and soluble salts thereof,
-(4'methylbenzylidene)-d,l-camphor,
3-benzylidene-d,l-camphor,
benzene 1,4-di(3-methylidene-10-camphosulfonic) acid and salts thereof (the product Mexoryl SX described in U.S. Pat. No. 4,585,597 issued to Lange et al. on Apr. 29, 1986, hereby incorporated by reference),
urocanic acid,
2,4,6-tris[p-(2'-ethyl hexyl-1'-oxycarbonyl)-anilino]-1,3,5-triazine,
2-[(p-(tertiobutylamido)anilino]4,6-bis-[(p-(2'-ethylhexyl-1'-oxycarbonyl)anilino]-1,3,5-triazine,
2,4-bis{[4-(2-ethyl-hexyloxy)]-2-hydroxy]-phenyl}-6-(4-methoxy-phenyl)-1,3,5-triazine ("TINOSORB S" marketed by Ciba),
the polymer of N-(2 et 4)-[(2-oxoborn-3-yliden)methyl]benzyl]-acrylamide,
1,4-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (Drometrizole Trisiloxane),
dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark TINOSORB M by Ciba-Geigy, and
solubilized 2,2'-methylene-bis-[6-(2H-benzotriazol-2-yl)-4-(methyl)phenol] such as that marketed under the trademark MIXXIM BB/200 by Fairmount Chemical.

Typically, combinations of one of more of these sunscreens are used.

The dibenzoyl methane derivatives other than avobenzone are described, for example, in FR-2,326,405, FR-2,440,933 and EP-0,114,607, hereby expressly incorporated by reference.

Other dibenzoyl methane sunscreens other than avobenzone include (whether singly or in any combination):
2-methyldibenzoylmethane
4-methyldibenzoylmethane
4-isopropyldibenzoylmethane
4-tert.-butyidibenzoylmethane
2,4-dimethyldibenzoylmethane
2,5-dimethyldibenzoylmethane
4,4'-diisopropyldibenzoylmethane
4,4'-dimethoxydibenzoylmethane
2-methyl-5-isopropyl-4'-methoxydibenzoylmethane
2-methyl-5-tert.-butyl-4'-methoxydibenzoylmethane
2,4-dimethyl-4'-methoxydibenzoylmethane
2,6-dimethyl-4-tert.-butyl-4'-methoxydibenzoylmethane Additional sunscreens that can be used are described in pages 2954-2955 of the *International Cosmetic Ingredient Dictionary and Handbook* (9$^{th}$ ed. 2002).

The sunscreens are generally present in the compositions according to the invention in proportions ranging from 0.1 to 30% by weight with respect to the total weight of the composition and preferably ranging from 0.2 to 15% by weight with respect to the total weight of the composition. Compositions of the invention preferably have a SPF of 30 and above, including 35, 40, 45, etc.

Fillers

According to the present invention, the compositions may further comprise at least one filler. As used herein, the term "filler" means any particle that is solid at room temperature and atmospheric pressure, used alone or in combination, which does not react chemically with the various ingredients of the emulsion and which is insoluble in these ingredients, even when these ingredients are raised to a temperature above room temperature and in particular to their softening point or their melting point. In an embodiment, the at least one filler has a melting point at least greater than 1700° C., for example, greater than 2000° C. In an embodiment, the at least one filler may have an apparent diameter ranging from 0.01 μm to 150 μm, such as from 0.5 μm to 120 μm, for example from 1 μm to 80 μm. An apparent diameter corresponds to the diameter of the circle into which the elementary particle fits along its shortest dimension (thickness for leaflets). Further, the at least one filler may be absorbent, i.e., capable in particular of absorbing the oils of the composition and also the biological substances secreted by the skin, may be surface-treated, e.g., to make it lipophilic, and/or may be porous so as to absorb the sweat and/or sebum secreted by the skin.

The at least one filler may be chosen from inorganic and organic fillers, and may have any shape such as lamellar, spherical and/or oblong. Non-limiting examples of the at least one inert filler include talc, mica, silica, kaolin, polyamide powders (such as Nylon® powder, and such as the product sold by Atochem as Orgasol®), poly-β-alanine powders, polyethylene powders, acrylic polymer powders (such as polymethyl methacrylate (PMMA) powder, for instance the product sold by Wacker as Covabead LH-85 (particle size 10-12 μm) and the acrylic acid copolymer powder sold by Dow Corning as Polytrap®), polytetrafluoroethylene (Teflon®) powders, lauroyllysine, boron nitride, silica, kaolin, starch, starch derivatives, hollow polymer microspheres (such as those hollow polymer microspheres formed from polyvinylidene chloride and acrylonitrile, for instance the product sold by Nobel Industrie as Expancel®), and polymerized silicone microspheres (such as those polymerized silicone microspheres sold by Toshiba as Tospearl®), precipitated calcium carbonate, magnesium carbonate and hydrocarbonate, hydroxyapatite, ceramic microcapsules, polyester particles and coated elastomers such as products sold under the denomination KSP (KSP100, KSP 200, KSP 300) sold by Shin Etsu and/or those described in U.S. Pat. No. 5,538,793, the disclosure of which is hereby incorporated by reference.

The composition according to the invention can be in the form of a tinted or non tinted dermatological composition or a care composition for keratin materials such as the skin, the lips and/or superficial body growths, in the form of an antisun composition or make-up-removing product in stick form. It can be used in particular as a care base for the skin, superficial body growths or the lips (lip balms, for protecting the lips against cold and/or sunlight and/or the wind, or care cream for the skin, the nails or the hair). As defined herein, a deodorant product is personal hygiene product and does not relate to care, make-up or treatment of keratin materials, including keratinous fibers.

The composition of the invention may also be in the form of a colored make-up product for the skin, in particular a foundation, optionally having care or treating properties, a blusher, a face powder, an eye shadow, a concealer product, an eyeliner, a make-up product for the body; a make-up product for the lips such as a lipstick, optionally having care or treating properties; a make-up product for superficial body growths such as the nails or the eyelashes, in particular in the form of a mascara cake, or for the eyebrows and the hair, in particular in the form of a pencil.

Needless to say, the composition of the invention should be cosmetically or dermatologically acceptable, i.e., it should contain a non-toxic physiologically acceptable medium and should be able to be applied to the skin, superficial body growths or the lips of human beings. For the purposes of the invention, the expression "cosmetically acceptable" means a composition of pleasant appearance, odor, feel and/or taste.

According to preferred embodiments of the present invention, methods of treating, caring for and/or making up keratinous material such as skin, lips, hair and mucous membranes by applying compositions of the present invention to the keratinous material in an amount sufficient to treat, care for and/or make up the keratinous material are provided.

According to other preferred embodiments, methods of covering or hiding defects associated with keratinous material such as imperfections or discolorations by applying compositions of the present invention to the keratinous material in an amount sufficient to cover or hide such defects are provided.

According to yet other preferred embodiments, methods of enhancing the appearance of keratinous material by applying compositions of the present invention to the keratinous material in an amount sufficient to enhance the appearance of the keratinous material are provided.

In accordance with the three preceding preferred embodiments, the compositions of the present invention are applied topically to the desired area of the skin in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects. The composition is preferably applied to the desired area that is dry or has been dried prior to application. Most preferably, the composition further comprises at least one film forming agent, at least one volatile oil, or a mixture thereof and/or pigments.

According to a preferred embodiment of the present invention, compositions having improved cosmetic properties such as, for example, improved long wear, transfer resistance or waterproof properties are provided. The improved properties may also be chosen from improved flexibility, wearability, drying time or retention as well as reduced tackiness or migration over time.

The present invention also envisages kits and/or prepackaged materials suitable for consumer use containing one or more compositions according to the description herein. The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, unless otherwise specified.

Example 1

Foundation

| Phase | Trade Name | INCI Name | % w/w |
|---|---|---|---|
| A | ISOLAN GI 34 | POLYGLYCERYL-4 ISOSTEARATE | 1.50 |
|   | ABIL EM 90 | CETYL PEG/PPG-10/1 DIMETHICONE | 1.00 |
|   | BELSIL DMC 6038 | BIS-PEG-15 METHYL ETHER DIMETHICONE | 0.80 |
|   | ITT-Titanium Dioxide | ITT-Titanium Dioxide | 10.20 |
|   | ITT-Iron Oxide - Yellow | ITT-Iron Oxides | 1.25 |
|   | ITT-Iron Oxide - Red | ITT-Iron Oxides (and) Iron Oxides | 0.40 |
|   | ITT-Iron Oxide - Black | ITT-Iron Oxides (and) Iron Oxides | 0.15 |
|   |   | Ethyl heptamethyl trisiloxane | 20.00 |
|   | DC fluid 200 200 cst | Dimethicone | 3.00 |
|   | SR-1000 | TRIMETHYLSILOXYSILICATE | 12.00 |
| B1 | SUNSPHERE H 51 | SILICA | 2.50 |
|   | MSS-500W | SILICA | 3.00 |
| B2 | Butylparaben | Butylparaben | 0.20 |
|   | Betone 38V | Disteardimonium Hectorite | 1.40 |
|   | Propylene Carbonate | Propylene Carbonate | 0.70 |
| C | Water | Water | 39.00 |
|   | SODIUM CHLORIDE | SODIUM CHLORIDE | 1.00 |
|   | HYDROLITE-5 | PENTYLENE GLYCOL | 0.50 |
|   | SODIUM DEHYDROACETATE MONOHYDRATE | SODIUM DEHYDROACETATE | 0.20 |
|   | Methylparaben | Methylparaben | 0.20 |
|   | BRIJ 30 | Laureth-4 | 0.50 |
|   | Phenoxyethanol | Phenoxyethanol | 0.50 |
|   |   | Total: | 100.00 |

Procedure:

1. Mix phase A ingredients, grinding with Silverson at 6000 to 7000 rpm for 30 to 40 min.

2. Add phase B1 ingredients one at a time, mix well with Silverson at about 6000 rpm.

3. Add butylparaben and Disteardimonium Hectorite, mixing with Silverson at 6000 rpm till good dispersion, then add Propylene Carbonate, mix at 6000 to 7000 rpm for 10-15 min.

4. Remove the main beaker from Silverson to Homogenizer. Warm the content to 25 to 30° C.

5. In a separate beaker, heat the phase C to 40 to 45. After uniform, cool the

6. Add phase C slowly to main beaker at 25 to 30° C. to form emulsion. Homogenize at 30% for 5 min.

Example 2

Lip Color Base

| Phase | Trade Name | INCI Name | % w/w |
|---|---|---|---|
| A1 |   | Butyl heptamethyl trisiloxane | 50.00 |
|   | DC fluid 200 200 cst | Dimethicone | 5.00 |
|   | SR-1000 | TRIMETHYLSILOXYSILICATE | 18.00 |
| A2 | Pigments and pearl | Pigment Mixture | 11.30 |
|   | SUNSPHERE H 51 | SILICA | 5.70 |
|   | Liquapar oil | ISOPROPYLPARABEN (and) ISOBUTYLPARABEN (and) BUTYLPARABEN | 0.20 |
|   | CARDRE MICA 8 | Mica | 4.20 |
| A3 | Betone 38V | Disteardimonium Hectorite | 3.70 |
|   | Propylene Carbonate | Propylene Carbonate | 1.90 |
|   |   | Total: | 100.00 |

Procedure:

1. Mix A1 at room temp to until uniform.

2. Add phase A2 ingredients one at a time, grinding with Silverson at 6000 to 7000 rpm for 60 min at room temperature.

3. Add Disteardimonium Hectorite of phase A3, disperse with Silverson at 6000 to 7000 rpm for 5-10 min. Until good dispersion. Then add Propylene Carbonate at same speed disperse for additional 10 min.

The present application claims priority from U.S. provisional patent application No. 60/528,696, filed Dec. 12, 2003, the entire disclosure of which is hereby incorporated by reference.

What is claimed is:

1. A method comprising:
   applying to the skin or lips a composition comprising:
   ethylheptamethyltrisiloxane and/or butylheptamethyltrisiloxane;
   at least one silicone resin; and
   a cosmetically acceptable medium.

2. The method according to claim 1, wherein the at least one silicone resin comprises a trialkylsiloxysilicate resin.

3. The method according to claim 2, wherein the trialkylsiloxysilicate is trimethylsiloxysilicate.

4. The method according to claim 1, wherein the composition further comprises at least one coloring agent selected from the group consisting of a pigment, a liposoluble dye, a nacreous pigment and a pearling agent.

5. The method according to claim 1, wherein the composition further comprises water.

6. The method according to claim 5, wherein the composition is an emulsion or a dispersion.

7. The method according to claim 1, wherein the composition is anhydrous.

8. The method according to claim 1, wherein the composition further comprises a surfactant.

9. The method according to claim 1, wherein the composition further comprises a volatile oil which is not ethylheptamethyltrisiloxane or butylheptamethyltrisiloxane.

10. The method according to claim 9, wherein a flash point of the volatile oil which is not ethylheptamethyltrisiloxane or butylheptamethyltrisiloxane is in the range of from 40 to 134° C.

11. The method according to claim 9, wherein the volatile oil which is not ethylheptamethyltrisiloxane or butylheptamethyltrisiloxane is at least one selected from the group consisting of octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane.

12. The method according to claim 9, wherein the volatile oil which is not ethylheptamethyltrisiloxane or butylheptamethyltrisiloxane is a volatile hydrocarbon oil.

13. The method according to claim 1, wherein a percent by weight relative to the total weight of the composition of the siloxysilicate resin is from about 1% to about 15%.

14. The method according to claim 1, wherein a percent by weight relative to the total weight of the composition of the ethylheptamethyltrisiloxane and/or butylheptamethyltrisiloxane is from about 1% to about 15%.

15. The method according to claim 1, wherein the siloxysilicate is diisostearoyl trimethylolpropane siloxysilicate or dilauroyl trimethylolpropane siloxy silicate.

16. The method according to claim 5, wherein a content of water in the composition is in a range of from 0.1 to 70% by weight relative to the total weight of the composition.

17. The method according to claim 4, wherein the at least one coloring agent is at least one pigment selected from the group of pigments consisting of titanium dioxide, zirconium oxide, zinc oxide, cerium oxide, iron oxide, chromium oxide, manganese violet, ultramarine blue, chromium hydrate, ferric blue, carbon black, a D & C pigment and a cochineal carmine lake.

18. The method according to claim 4, wherein the at least one coloring agent is at least one liposoluble dye selected from the group consisting of Sudan Red, DC Red 17, DC Green 6, β-carotene, soybean oil, Sudan Brown, DC Yellow 11, DC Violet 2, DC Orange 5, annatto and quinoline yellow.

19. The method according to claim 4, wherein the at least one coloring agent is at least one nacreous pigment selected from the group consisting of a mica coated with titanium, a mica coated with bismuth oxychloride, a titanium mica coated with an iron oxide, a titanium mica coated with ferric blue, a titanium mica coated with chromium oxide and a titanium mica coated with an organic pigment.

* * * * *